United States Patent
Hansen et al.

(10) Patent No.: US 11,667,660 B2
(45) Date of Patent: Jun. 6, 2023

(54) PYRIDINIUM SALTS AS ACTIVATORS IN THE SYNTHESIS OF STEREODEFINED OLIGONUCLEOTIDES

(71) Applicant: ROCHE INNOVATION CENTER COPENHAGEN A/S, Hørsholm (DK)

(72) Inventors: Dennis Jul Hansen, Farum (DK); Erik Daa Funder, Hilleroed (DK)

(73) Assignee: Roche Innovation Center Copenhagen A/S, Horsholm (DK)

( * ) Notice: Subject to any disclaimer, the term of this patent is extended or adjusted under 35 U.S.C. 154(b) by 0 days.

(21) Appl. No.: 17/241,535

(22) Filed: Apr. 27, 2021

(65) Prior Publication Data

US 2021/0355150 A1    Nov. 18, 2021

Related U.S. Application Data

(63) Continuation of application No. PCT/EP2019/081864, filed on Nov. 20, 2019.

(30) Foreign Application Priority Data

Nov. 22, 2018    (EP) .................... 18207887

(51) Int. Cl.
    *C07H 1/02*      (2006.01)
    *C07H 19/213*    (2006.01)

(52) U.S. Cl.
    CPC ............. *C07H 1/02* (2013.01); *C07H 19/213* (2013.01)

(58) Field of Classification Search
    None
    See application file for complete search history.

(56) References Cited

FOREIGN PATENT DOCUMENTS

| WO | 99/62922 A1 | 12/1999 | |
|---|---|---|---|
| WO | WO-1999062922 | * 12/1999 | .............. C07H 1/00 |
| WO | 2017/194498 A1 | 11/2017 | |
| WO | 2018/019799 A2 | 2/2018 | |
| WO | 2018/177825 A1 | 10/2018 | |
| WO | WO-2018177825 A1 | * 10/2018 | .............. C07H 1/00 |

OTHER PUBLICATIONS

Guo, M., et al., "Solid-phase stereoselective synthesis of 2'-O-methyl-oligoribonucleoside phosphorothioates using nucleoside bicyclic oxazaphospholidines", Bioorg. Med. Chem. Lett., , 8: 2539-2544 (1998).
International Preliminary Report on Patentability received for PCT Patent Application No. PCT/EP2019/081864, dated Jun. 3, 2021, 10 pages.
International Search Report and Written Opinion received for PCT Patent Application No. PCT/EP2019/081864, dated Feb. 4, 2020, 14 pages.
Oka, N., et al., "Stereocontrolled synthesis of oligoribonucleoside phosphorothioates by an oxazaphospholidine approach", Org. Lett., 11(4): 967-970 (2009).
Singh, S.K., et al., "LNA (locked nucleic acids): synthesis and high-affinity nucleic acid recognition", J. Chem. Commun., 4:455-456 (1998).

* cited by examiner

*Primary Examiner* — Traviss C McIntosh, III
(74) *Attorney, Agent, or Firm* — Smith Gambrell & Russell LLP; Judy Jarecki-Black; Ram W. Sabnis

(57) ABSTRACT

The present invention relates to a method for preparing stereodefined phosphorothioate oligonucleotides, especially locked stereodefined phosphorothioate oligonucleotides with a high yield, using pyridinium acidic salts as a coupling activator.

17 Claims, 8 Drawing Sheets

A  1M DCI+0,1M NMI

B  0,50M Pyridine hydrochloride

C  0,25M Pyridine hydrochloride

D  0,25M Pyridine hydrobromide

FIGURES 5A-B
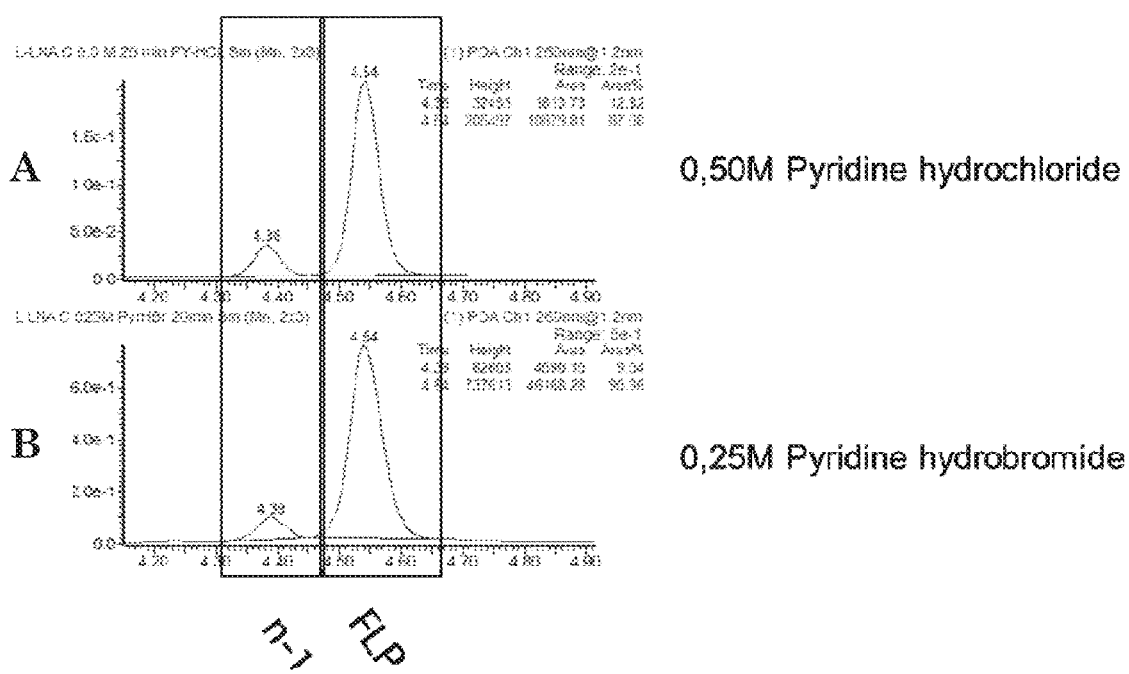

FIGURES 6A-E
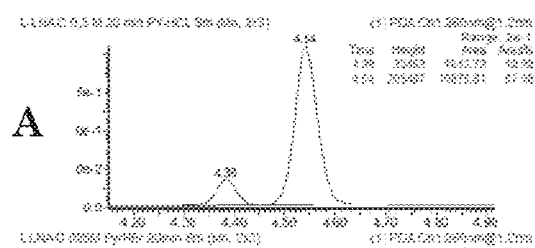
0.50M Pyridine hydrochloride
0.25M Pyridine hydrobromide
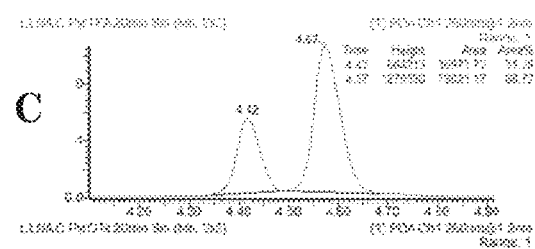
0.25M Pyridinium Trifluoroacetate
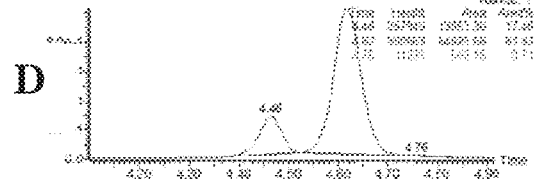
0.25M Pyridinium p-toluene sulfonate
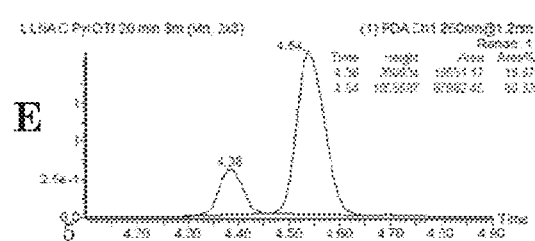
0.25M Pyridinium triflate

PYRIDINIUM SALTS AS ACTIVATORS IN THE SYNTHESIS OF STEREODEFINED OLIGONUCLEOTIDES

The invention relates to a novel process for preparing stereodefined oligonucleotides.

The use of synthetic oligonucleotides as therapeutic agents has witnessed remarkable progress over recent decades leading to the development of molecules acting by diverse mechanisms including RNase H activating gapmers, splice switching oligonucleotides, microRNA inhibitors, siRNA or aptamers (S. T. Crooke, *Antisense drug technology: principles, strategies, and applications*, 2nd ed. ed., Boca Raton, Fla.: CRC Press, 2008).

Synthesis of LNA (Locked Nucleic Acid) monomers were first reported by Wengel et al (Singh, S. K., Nielsen, P., Koshkin, A. A. and Wengel, J. Chem. Commun., 1998, 455.

Nathsuhisa Oka et al. describe the synthesis of phosphorothioate oligonucleotides in Org. Lett., Vol. 11, No. 4, 2009. The synthesis described by Oka et al. is performed on a solid support testing various coupling activators. Oka et al. show that N-phenyl imidazolium triflate is the best activator. Unfortunately, Oka et al. did not explore the synthesis of stereodefined phosphorothioate modified oligonucleotides or such as Locked Nucleic Acids (LNAs).

MaoJun Guo et al. describe the synthesis of 2'-O-Methyl-phosphorothiotate oligonucleotide using 1H-tetrazole as activator in Bioorg. Med. Chem. Lett. 8 (1998) 2539-2544. Unfortunately, Guo et al. is does not offer guidance at to the synthesis of stereodefined phosphorothioate oligonucleotides.

A review of the literature shows that it remains scarce on the synthesis of stereodefined modified oligonucleotides. However, the inventors believe that stereodefined oligonucleotides will lead to oligonucleotides with better pharmacological properties. As per their chemical structure, oligonucleotides inherently have many stereocenters, in particular on the phosphate atom of their internucleoside linkages. These stereocenters mean that a given oligonucleotide is actually a mixture of oligonucleotide stereoisomers. The inventors have observed that pharmacological properties of given mixture of oligonucleotide stereoisomers can be improved by selecting those stereoisomers that have better pharmacological properties than others in the mixture. The inventors are therefore interested in synthesizing and/or selecting stereoisomers that have mover favorable pharmacological properties over the others.

However, despite various attempts to further the synthesis of oligonucleotides, there is still a need for a synthesis of stereodefined phosphorothioate oligonucleotides, especially stereodefined locked phosphorothioate oligonucleotides such as LNAs (Locked Nucleic Acids) with a high yield.

The inventors were surprised to find a novel process for preparing stereodefined phosphorothioate oligonucleotides, especially locked phosphorothioate oligonucleotides with a high yield, using pyridinium acidic salts as a coupling activator. Further key improvements for the process according to the invention over the art will be outlined hereinbelow.

SUMMARY OF THE INVENTION

In one aspect, the invention relates to a method for preparing stereodefined phosphorothioate oligonucleotides, especially locked stereodefined phosphorothioate oligonucleotides with a relative high yield, using pyridinium acidic salts as a coupling activator.

In another aspect, the invention relates to a composition comprising a pyridinium acidic salt activator, a solvent and a monomer for the preparation of stereodefined phosphorothioate oligonucleotides with a pyridinium acidic salt activator.

In yet another aspect, the invention relates to the use of a pyridinium acidic salt as a coupling activator in the preparation of modified stereodefined phosphorothioate oligonucleotides.

Definitions

The term "alkyl", alone or in combination, signifies a straight-chain or branched-chain alkyl group with 1 to 8 carbon atoms, particularly a straight or branched-chain alkyl group with 1 to 6 carbon atoms and more particularly a straight or branched-chain alkyl group with 1 to 4 carbon atoms. Examples of straight-chain and branched-chain $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, particularly methyl, ethyl, propyl, butyl and pentyl. Particular examples of alkyl are methyl, ethyl and propyl.

The term "cycloalkyl", alone or in combination, signifies a cycloalkyl ring with 3 to 8 carbon atoms and particularly a cycloalkyl ring with 3 to 6 carbon atoms. Examples of cycloalkyl are cyclopropyl, cyclobutyl, cyclopentyl, cyclohexyl, cycloheptyl and cyclooctyl, more particularly cyclopropyl and cyclobutyl. A particular example of "cycloalkyl" is cyclopropyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec.butoxy and tert.butoxy. Particular "alkoxy" are methoxy and ethoxy. Methoxyethoxy is a particular example of "alkoxyalkoxy".

The term "oxy", alone or in combination, signifies the —O— group.

The term "alkenyl", alone or in combination, signifies a straight-chain or branched hydrocarbon residue comprising an olefinic bond and up to 8, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl and isobutenyl.

The term "alkynyl", alone or in combination, signifies a straight-chain or branched hydrocarbon residue comprising a triple bond and up to 8, particularly 2 carbon atoms.

The terms "halogen" or "halo", alone or in combination, signifies fluorine, chlorine, bromine or iodine and particularly fluorine, chlorine or bromine, more particularly fluorine. The term "halo", in combination with another group, denotes the substitution of said group with at least one halogen, particularly substituted with one to five halogens, particularly one to four halogens, i.e. one, two, three or four halogens.

The term "haloalkyl", alone or in combination, denotes an alkyl group substituted with at least one halogen, particularly substituted with one to five halogens, particularly one to three halogens. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl or trifluoromethyl. Fluoromethyl, difluoromethyl and trifluoromethyl are particular "haloalkyl".

The term "halocycloalkyl", alone or in combination, denotes a cycloalkyl group as defined above substituted with at least one halogen, particularly substituted with one to five halogens, particularly one to three halogens. Particular example of "halocycloalkyl" are halocyclopropyl, in particular fluorocyclopropyl, difluorocyclopropyl and trifluorocyclopropyl.

The terms "hydroxyl" and "hydroxy", alone or in combination, signify the —OH group.

The terms "thiohydroxyl" and "thiohydroxy", alone or in combination, signify the —SH group.

The term "carbonyl", alone or in combination, signifies the —C(O)— group.

The term "carboxy" or "carboxyl", alone or in combination, signifies the —COOH group.

The term "amino", alone or in combination, signifies the primary amino group (—NH$_2$), the secondary amino group (—NH—), or the tertiary amino group (—N—).

The term "alkylamino", alone or in combination, signifies an amino group as defined above substituted with one or two alkyl groups as defined above.

The term "sulfonyl", alone or in combination, means the —SO$_2$ group.

The term "sulfinyl", alone or in combination, signifies the —SO— group.

The term "sulfanyl", alone or in combination, signifies the —S— group.

The term "cyano", alone or in combination, signifies the —CN group.

The term "azido", alone or in combination, signifies the —N$_3$ group.

The term "nitro", alone or in combination, signifies the NO$_2$ group.

The term "formyl", alone or in combination, signifies the —C(O)H group.

The term "carbamoyl", alone or in combination, signifies the —C(O)NH$_2$ group.

The term "cabamido", alone or in combination, signifies the —NH—C(O)—NH$_2$ group.

The term "aryl", alone or in combination, denotes a monovalent aromatic carbocyclic mono- or bicyclic ring system comprising 6 to 10 carbon ring atoms, optionally substituted with 1 to 3 substituents independently selected from halogen, hydroxyl, alkyl, alkenyl, alkynyl, alkoxy, alkoxyalkyl, alkenyloxy, carboxyl, alkoxycarbonyl, alkylcarbonyl and formyl. Examples of aryl include phenyl and naphthyl, in particular phenyl.

The term "heteroaryl", alone or in combination, denotes a monovalent aromatic heterocyclic mono- or bicyclic ring system of 5 to 12 ring atoms, comprising 1, 2, 3 or 4 heteroatoms selected from N, O and S, the remaining ring atoms being carbon, optionally substituted with 1 to 3 substituents independently selected from halogen, hydroxyl, alkyl, alkenyl, alkynyl, alkoxy, alkoxyalkyl, alkenyloxy, carboxyl, alkoxycarbonyl, alkylcarbonyl and formyl. Examples of heteroaryl include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzoxadiazolyl, benzothiadiazolyl, benzotriazolyl, purinyl, quinolinyl, isoquinolinyl, quinazolinyl, quinoxalinyl, carbazolyl or acridinyl.

The term "heterocyclyl", alone or in combination, signifies a monovalent saturated or partly unsaturated mono- or bicyclic ring system of 4 to 12, in particular 4 to 9 ring atoms, comprising 1, 2, 3 or 4 ring heteroatoms selected from N, O and S, the remaining ring atoms being carbon, optionally substituted with 1 to 3 substituents independently selected from halogen, hydroxyl, alkyl, alkenyl, alkynyl, alkoxy, alkoxyalkyl, alkenyloxy, carboxyl, alkoxycarbonyl, alkylcarbonyl and formyl. Examples for monocyclic saturated heterocyclyl are azetidinyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-azabicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl or dihydropyranyl.

The term "silyl" refer to a —SiH$_3$ group or any similar group in which one or more of the hydrogen atoms are replaced by organic groups. An example of such similar group is —SiMe(Ph)$_2$. The expression "silyl substituted by one or more substituent selected from C$_{1-4}$-alkyl and C$_{6-14}$ aryl" means a silyl group in which one or more of the hydrogen atoms are replaced by organic groups selected from C$_{1-4}$-alkyl and C$_{6-14}$ aryl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, particularly hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein. In addition these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins. The oligonucleotide of the invention can also be present in the form of zwitterions. Particularly preferred pharmaceutically acceptable salts of the invention are the sodium, lithium, potassium and trialkylammonium salts.

The term "protecting group", alone or in combination, signifies a group, which selectively blocks a reactive site in a multifunctional compound such that a chemical reaction can be carried out selectively at another unprotected reactive site. Protecting groups can be removed. Exemplary protecting groups are amino-protecting groups, carboxy-protecting groups or hydroxy-protecting groups.

"Phosphate protecting group" is a protecting group of the phosphate group. Examples of phosphate protecting group are 2-cyanoethyl and methyl A particular example of phosphate protecting group is 2-cyanoethyl.

"Hydroxyl protecting group" is a protecting group of the hydroxyl group and is also used to protect thiol groups. Examples of hydroxyl protecting groups are acetyl (Ac), benzoyl (Bz), benzyl (Bn), β-methoxyethoxymethyl ether (MEM), dimethoxytrityl (or bis-(4-methoxyphenyl)phenylmethyl) (DMT), trimethoxytrityl (or tris-(4-methoxyphenyl) phenylmethyl) (TMT), methoxymethyl ether (MOM), methoxytrityl [(4-methoxyphenyl)diphenylmethyl (MMT), p-methoxybenzyl ether (PMB), methylthiomethyl ether, pivaloyl (Piv), tetrahydropyranyl (THP), tetrahydrofuran (THF), trityl or triphenylmethyl (Tr), silyl ether (for example trimethylsilyl (TMS), tert-butyldimethylsilyl (TBDMS), tri-iso-propylsilyloxymethyl (TOM) and triisopropylsilyl (TIPS) ethers), methyl ethers and ethoxyethyl ethers (EE). Particular examples of hydroxyl protecting group are DMT and TMT, in particular DMT.

"Thiohydroxyl protecting group" is a protecting group of the thiohydroxyl group. Examples of thiohydroxyl protecting groups are those of the "hydroxyl protecting group".

If one of the starting materials or compounds of the invention contain one or more functional groups which are not stable or are reactive under the reaction conditions of one or more reaction steps, appropriate protecting groups (as described e.g. in "Protective Groups in Organic Chemistry" by T. W. Greene and P. G. M. Wuts, $3^{rd}$ Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethylsilylethyl carbamate (Teoc), carbobenzyloxy (Cbz) and p-methoxybenzyloxycarbonyl (Moz).

The compounds described herein can contain several asymmetric centers and can be present in the form of optically pure enantiomers, mixtures of enantiomers such as, for example, racemates, mixtures of diastereoisomers, diastereoisomeric racemates or mixtures of diastereoisomeric racemates.

Oligonucleotide

The term "oligonucleotide" as used herein is defined as it is generally understood by the skilled person as a molecule comprising two or more covalently linked nucleosides. Such covalently bound nucleosides may also be referred to as nucleic acid molecules or oligomers. Oligonucleotides are commonly made in the laboratory by solid-phase chemical synthesis followed by purification. When referring to a sequence of the oligonucleotide, reference is made to the sequence or order of nucleobase moieties, or modifications thereof, of the covalently linked nucleotides or nucleosides. The oligonucleotide of the invention is man-made, and is chemically synthesized, and is typically purified or isolated. The oligonucleotide of the invention may comprise one or more modified nucleosides or nucleotides.

Antisense Oligonucleotides

The term "Antisense oligonucleotide" as used herein is defined as oligonucleotides capable of modulating expression of a target gene by hybridizing to a target nucleic acid, in particular to a contiguous sequence on a target nucleic acid. The antisense oligonucleotides are not essentially double stranded and are therefore not siRNAs or shRNAs. Preferably, the antisense oligonucleotides of the present invention are single stranded. It is understood that single stranded oligonucleotides of the present invention can form hairpins or intermolecular duplex structures (duplex between two molecules of the same oligonucleotide), as long as the degree of intra or inter self-complementarity is less than 50% across of the full length of the oligonucleotide.

Contiguous Nucleotide Sequence

The term "contiguous nucleotide sequence" refers to the region of the oligonucleotide which is complementary to the target nucleic acid. The term is used interchangeably herein with the term "contiguous nucleobase sequence" and the term "oligonucleotide motif sequence". In some embodiments all the nucleotides of the oligonucleotide constitute the contiguous nucleotide sequence. In some embodiments the oligonucleotide comprises the contiguous nucleotide sequence, such as a F-G-F' gapmer region, and may optionally comprise further nucleotide(s), for example a nucleotide linker region which may be used to attach a functional group to the contiguous nucleotide sequence. The nucleotide linker region may or may not be complementary to the target nucleic acid.

Nucleotides

Nucleotides are the building blocks of oligonucleotides and polynucleotides and for the purposes of the present invention include both naturally occurring and non-naturally occurring nucleotides. In nature, nucleotides, such as DNA and RNA nucleotides comprise a ribose sugar moiety, a nucleobase moiety and one or more phosphate groups (which is absent in nucleosides). Nucleosides and nucleotides may also interchangeably be referred to as "units" or "monomers".

Modified Nucleoside

The term "modified nucleoside" or "nucleoside modification" as used herein refers to nucleosides modified as compared to the equivalent DNA or RNA nucleoside by the introduction of one or more modifications of the sugar moiety or the (nucleo)base moiety. In a preferred embodiment the modified nucleoside comprise a modified sugar moiety. The term modified nucleoside may also be used herein interchangeably with the term "nucleoside analogue" or modified "units" or modified "monomers". Nucleosides with an unmodified DNA or RNA sugar moiety are termed DNA or RNA nucleosides herein. Nucleosides with modifications in the base region of the DNA or RNA nucleoside are still generally termed DNA or RNA if they allow Watson Crick base pairing.

Nucleobase

The term nucleobase includes the purine (e.g. adenine and guanine) and pyrimidine (e.g. uracil, thymine and cytosine) moieties present in nucleosides and nucleotides which form hydrogen bonds in nucleic acid hybridization. In the context of the present invention, the term nucleobase also encompasses modified nucleobases, which may differ from naturally occurring nucleobases, but are functional during nucleic acid hybridization. In this context, "nucleobase" refers to both naturally occurring nucleobases such as adenine, guanine, cytosine, thymidine, uracil, xanthine and hypoxanthine, as well as non-naturally occurring variants. Such variants are for example described in Hirao et al (2012) Accounts of Chemical Research vol. 45 page 2055 and Bergstrom (2009) Current Protocols in Nucleic Acid Chemistry Suppl. 37 1.4.1.

In some embodiments the nucleobase moiety is modified by changing the purine or pyrimidine into a modified purine or pyrimidine, such as substituted purine or substituted pyrimidine, such as a nucleobase selected from isocytosine, pseudoisocytosine, 5-methyl cytosine, 5-thiozolo-cytosine, 5-propynyl-cytosine, 5-propynyl-uracil, 5-bromouracil 5-thiazolo-uracil, 2-thio-uracil, 2'thio-thymine, inosine, diaminopurine, 6-aminopurine, 2-aminopurine, 2,6-diaminopurine and 2-chloro-6-aminopurine.

The nucleobase moieties may be indicated by the letter code for each corresponding nucleobase, e.g. A, T. G. C or U, wherein each letter may optionally include modified nucleobases of equivalent function. For example, in the exemplified oligonucleotides, the nucleobase moieties are selected from A, T, G, C, and 5-methyl cytosine. Optionally, for LNA gapmers, 5-methyl cytosine LNA nucleosides may be used.

5'-Hydroxyl Protected Nucleoside

The conventional chemical nomenclature for nucleosides is as depicted below. In the expression a "5'-hydroxyl protected nucleosides", the 5' position to which it is referred is as depicted below wherein PGO is a hydroxyl protecting group and B a nucleobase.

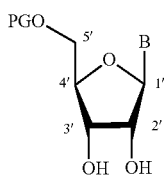

It is to be understood that the above representation solely serves the purpose of illustration of the 5' position. Many different nucleosides fall under the expression "5'-hydroxyl protected nucleosides" including modified nucleosides such as sugar-modified nucleosides as described herein.

Modified Oligonucleotide

The term modified oligonucleotide describes an oligonucleotide comprising one or more sugar-modified nucleosides and/or modified internucleoside linkages. The term chimeric" oligonucleotide is a term that has been used in the literature to describe oligonucleotides with modified nucleosides.

Stereodefined Oligonucleotide

A stereodefined oligonucleotide is an oligonucleotide wherein at least one of the internucleoside linkages is a stereodefined internucleoside linkage.

A stereodefined phosphorothioate oligonucleotide is an oligonucleotide wherein at least one of the internucleoside linkages is a stereodefined phosphorothioate internucleoside linkage.

Complementarity

The term "complementarity" describes the capacity for Watson-Crick base-pairing of nucleosides/nucleotides. Watson-Crick base pairs are guanine (G)-cytosine (C) and adenine (A)—thymine (T)/uracil (U). It will be understood that oligonucleotides may comprise nucleosides with modified nucleobases, for example 5-methyl cytosine is often used in place of cytosine, and as such the term complementarity encompasses Watson Crick base-paring between non-modified and modified nucleobases (see for example Hirao et al (2012) Accounts of Chemical Research vol. 45 page 2055 and Bergstrom (2009) Current Protocols in Nucleic Acid Chemistry Suppl. 37 1.4.1).

The term "% complementary" as used herein, refers to the proportion of nucleotides in a contiguous nucleotide sequence in a nucleic acid molecule (e.g. oligonucleotide) which, at a given position, are complementary to (i.e. form Watson Crick base pairs with) a contiguous nucleotide sequence, at a given position of a separate nucleic acid molecule (e.g. the target nucleic acid). The percentage is calculated by counting the number of aligned bases that form pairs between the two sequences (when aligned with the target sequence 5'-3' and the oligonucleotide sequence from 3'-5'), dividing by the total number of nucleotides in the oligonucleotide and multiplying by 100. In such a comparison, a nucleobase/nucleotide which does not align (form a base pair) is termed a mismatch. Preferably, insertions and deletions are not allowed in the calculation of percentage of complementarity of a contiguous nucleotide sequence.

The term "fully complementary", refers to 100% complementarity.

Identity

The term "Identity" as used herein, refers to the number of nucleotides in percent of a contiguous nucleotide sequence in a nucleic acid molecule (e.g. oligonucleotide) which, at a given position, are identical to (i.e. in their ability to form Watson Crick base pairs with the complementary nucleoside) a contiguous nucleotide sequence, at a given position of a separate nucleic acid molecule (e.g. the target nucleic acid) The percentage is calculated by counting the number of aligned bases that are identical between the two sequences dividing by the total number of nucleotides in the oligonucleotide and multiplying by 100. Percent Identity= (Matches×100)/Length of aligned region. Preferably, insertions and deletions are not allowed in the calculation of % complementarity of a contiguous nucleotide sequence.

Hybridization

The term "hybridizing" or "hybridizes" as used herein is to be understood as two nucleic acid strands (e.g. an oligonucleotide and a target nucleic acid) forming hydrogen bonds between base pairs on opposite strands thereby forming a duplex. The affinity of the binding between two nucleic acid strands is the strength of the hybridization. It is often described in terms of the melting temperature ($T_m$) defined as the temperature at which half of the oligonucleotides are duplexed with the target nucleic acid. At physiological conditions $T_m$ is not strictly proportional to the affinity (Mergny and Lacroix, 2003, *Oligonucleotides* 13:515-537). The standard state Gibbs free energy $\Delta G°$ is a more accurate representation of binding affinity and is related to the dissociation constant ($K_d$) of the reaction by $\Delta G°=-RTln(K_d)$, where R is the gas constant and T is the absolute temperature. Therefore, a very low $\Delta G°$ of the reaction between an oligonucleotide and the target nucleic acid reflects a strong hybridization between the oligonucleotide and target nucleic acid. $\Delta G°$ is the energy associated with a reaction where aqueous concentrations are 1M, the pH is 7, and the temperature is 37° C. The hybridization of oligonucleotides to a target nucleic acid is a spontaneous reaction and for spontaneous reactions $\Delta G°$ is less than zero. $\Delta G°$ can be measured experimentally, for example, by use of the isothermal titration calorimetry (ITC) method as described in Hansen et al., 1965, *Chem. Comm.* 36-38 and Holdgate et al., 2005, *Drug Discov Today*. The skilled person will know that commercial equipment is available for $\Delta G°$ measurements. $\Delta G°$ can also be estimated numerically by using the nearest neighbor model as described by SantaLucia, 1998, *Proc Natl Acad Sci USA*. 95: 1460-1465 using appropriately derived thermodynamic parameters described by Sugimoto et al., 1995, *Biochemistry* 34:11211-11216 and McTigue et al., 2004, *Biochemistry* 43:5388-5405. In order to have the possibility of modulating its intended nucleic acid target by hybridization, oligonucleotides of the present invention hybridize to a target nucleic acid with estimated $\Delta G°$ values below −10 kcal for oligonucleotides that are 10-30 nucleotides in length. In some embodiments the degree or strength of hybridization is measured by the standard state Gibbs free energy $\Delta G°$. The oligonucleotides may hybridize to a target nucleic acid with estimated $\Delta G°$ values below the range of −10 kcal, such as below −15 kcal, such as below −20 kcal and such as below −25 kcal for oligonucleotides that are 8-30 nucleotides in length. In some embodiments the oligonucleotides hybridize to a target nucleic acid with an estimated ΔG° value of −10 to −60 kcal, such as −12 to −40, such as from −15 to −30 kcal or −16 to −27 kcal such as −18 to −25 kcal.

Sugar Modifications

The oligomer of the invention may comprise one or more nucleosides, which have a modified sugar moiety, i.e. a modification of the sugar moiety when compared to the ribose sugar moiety found in DNA and RNA.

Numerous nucleosides with modification of the ribose sugar moiety have been made, primarily with the aim of improving certain properties of oligonucleotides, such as affinity and/or nuclease resistance. Such oligonucleotides are referred to a sugar modified nucleotides.

Such modifications include those where the ribose ring structure is modified, e.g. by replacement with a hexose ring (HNA), or a bicyclic ring, which typically have a biradical bridge between the C2 and C4 carbons on the ribose ring (LNA), or an unlinked ribose ring which typically lacks a bond between the C2 and C3 carbons (e.g. UNA). Other sugar-modified nucleosides include, for example, bicyclohexose nucleic acids (WO 2011/017521) or tricyclic nucleic acids (WO 2013/154798). Modified nucleosides also include nucleosides where the sugar moiety is replaced with a non-sugar moiety, for example in the case of peptide nucleic acids (PNA), or morpholino nucleic acids.

Sugar modifications also include modifications made via altering the substituent groups on the ribose ring to groups other than hydrogen, or the 2'-OH group naturally found in DNA and RNA nucleosides. Substituents may, for example be introduced at the 2', 3', 4' or 5' positions.

2' Sugar Modified Nucleosides.

A 2' sugar modified nucleoside is a nucleoside which has a substituent other than H or —OH at the 2' position (2' substituted nucleoside) or comprises a 2' linked biradical capable of forming a bridge between the 2' carbon and a second carbon in the ribose ring, such as LNA (2'-4' biradical bridged) nucleosides.

Indeed, much focus has been spent on developing 2' modified nucleosides, and numerous 2' modified nucleosides have been found to have beneficial properties when incorporated into oligonucleotides. For example, the 2' modified sugar may provide enhanced binding affinity and/or increased nuclease resistance to the oligonucleotide. Examples of 2' substituted modified nucleosides are 2'-O-alkyl-RNA, 2'-O-methyl-RNA, 2'-alkoxy-RNA, 2'-O-methoxyethyl-RNA (MOE), 2'-amino-DNA, 2'-fluoro-RNA and 2'-F-ANA nucleoside. Further examples can be found in e.g. Freier & Altmann; Nucl. Acid Res., 1997, 25, 4429-4443 and Uhlmann; Curr. Opinion in Drug Development, 2000, 3(2), 293-213 and Deleavey and Damha, Chemistry and Biology 2012, 19, 937. Below are illustrations of some 2' substituted modified nucleosides.

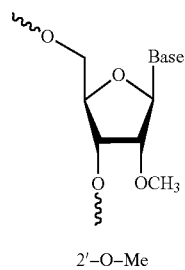

2'-O-Me

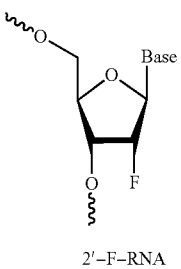

2'-F-RNA

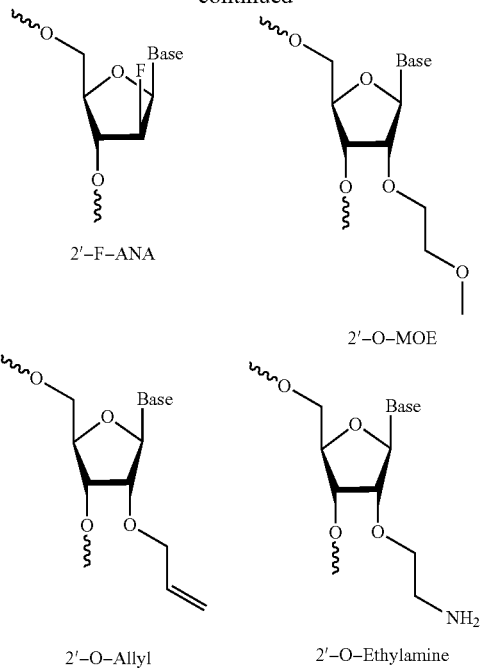

2'-F-ANA

2'-O-MOE

2'-O-Allyl

2'-O-Ethylamine

In relation to the present invention 2' modified does not include 2' bridged molecules like LNA.

Locked Nucleic Acid Nucleosides (LNA Nucleosides)

A "LNA nucleoside" is a 2'-modified nucleoside which comprises a biradical linking the C2' and C4' of the ribose sugar ring of said nucleoside (also referred to as a "2'-4' bridge"), which restricts or locks the conformation of the ribose ring. These nucleosides are also termed bridged nucleic acid or bicyclic nucleic acid (BNA) in the literature. The locking of the conformation of the ribose is associated with an enhanced affinity of hybridization (duplex stabilization) when the LNA is incorporated into an oligonucleotide for a complementary RNA or DNA molecule. This can be routinely determined by measuring the melting temperature of the oligonucleotide/complement duplex.

Non limiting, exemplary LNA nucleosides are disclosed in WO 99/014226, WO 00/66604, WO 98/039352, WO 2004/046160, WO 00/047599, WO 2007/134181, WO 2010/077578, WO 2010/036698, WO 2007/090071, WO 2009/006478, WO 2011/156202, WO 2008/154401, WO 2009/067647, WO 2008/150729, Morita et al., Bioorganic & Med. Chem. Lett. 12, 73-76, Seth et al. J. Org. Chem. 2010, Vol 75(5) pp. 1569-81 and Mitsuoka et al., Nucleic Acids Research 2009, 37(4), 1225-1238.

The 2'-4' bridge comprises 2 to 4 bridging atoms and is in particular of formula —X—Y—, Y being linked to C4' and X linked to C2', wherein X is oxygen, sulfur, —CR$^a$R$^b$—, —C(R$^a$)=C(R$^b$)—, —C(=CR$^a$R$^b$)—, —C(R$^a$)=N—, —Si(R$^a$)$_2$—, —SO$_2$—, —NR$^a$—; —O—NR$^a$—, —NR$^a$—O—, —C(=J)-, Se, —O—NR$^a$—, —NR$^a$—CR$^a$R$^b$—, —N(R$^a$)—O— or —O—CR$^a$R$^b$—;

Y is oxygen, sulfur, —(CR$^a$R$^b$)$_n$—, —CR$^a$R$^b$—O—CR$^a$R$^b$—, —C(R$^a$)=C(R$^b$)—, —C(R$^a$)=N—, —Si(R$^a$)$_2$—, —SO$_2$—, —NR$^a$—, —C(=J)-, Se, —O—NR$^a$—, —NR$^a$—CR$^a$R$^b$—, —N(R$^a$)—O— or —O—CR$^a$R$^b$—;

with the proviso that —X—Y— is not —O—O—, Si(R$^a$)$_2$—Si(R$^a$)$_2$—, —SO$_2$—SO$_2$—, —C(R$^a$)=C(R$^b$)—C(R$^a$)=C(R$^b$), —C(R$^a$)=N—C(R$^a$)=N—, —C(R$^a$)=N—C(R$^a$)=C(R$^b$), —C(R$^a$)=C(R$^b$)—C(R$^a$)=N— or —Se—Se—;

J is oxygen, sulfur, =CH$_2$ or =N(R$^a$);

R$^a$ and R$^b$ are independently selected from hydrogen, halogen, hydroxyl, cyano, thiohydroxyl, alkyl, substituted alkyl, alkenyl, substituted alkenyl, alkynyl, substituted alkynyl, alkoxy, substituted alkoxy, alkoxyalkyl, alkenyloxy, carboxyl, alkoxycarbonyl, alkylcarbonyl, formyl, aryl, heterocyclyl, amino, alkylamino, carbamoyl, alkylaminocarbonyl, aminoalkylaminocarbonyl, alkylaminoalkylaminocarbonyl, alkylcarbonylamino, carbamido, alkanoyloxy, sulfonyl, alkylsulfonyloxy, nitro, azido, thiohydroxylsulfidealkylsulfanyl, aryloxycarbonyl, aryloxy, arylcarbonyl, heteroaryl, heteroaryloxycarbonyl, heteroaryloxy, heteroarylcarbonyl, —OC(=X$^a$)R$^c$, —OC(=X$^a$)NR$^c$R$^d$ and —NR$^c$C(=X$^a$)NR$^c$R$^d$;

or two geminal R$^a$ and R$^b$ together form optionally substituted methylene;

or two geminal R$^a$ and R$^b$, together with the carbon atom to which they are attached, form cycloalkyl or halocycloalkyl, with only one carbon atom of —X—Y—;

wherein substituted alkyl, substituted alkenyl, substituted alkynyl, substituted alkoxy and substituted methylene are alkyl, alkenyl, alkynyl and methylene substituted with 1 to 3 substituents independently selected from halogen, hydroxyl, alkyl, alkenyl, alkynyl, alkoxy, alkoxyalkyl, alkenyloxy, carboxyl, alkoxycarbonyl, alkylcarbonyl, formyl, heterocylyl, aryl and heteroaryl;

X$^a$ is oxygen, sulfur or —NR$^c$;

R$^c$, R$^d$ and R$^e$ are independently selected from hydrogen and alkyl; and n is 1, 2 or 3.

In a further particular embodiment of the invention, X is oxygen, sulfur, —NR$^a$—, —CR$^a$R$^b$— or —C(=CR$^a$R$^b$)—, particularly oxygen, sulfur, —NH—, —CH$_2$— or —C(=CH$_2$)—, more particularly oxygen.

In another particular embodiment of the invention, Y is —CR$^a$R$^b$—, —CR$^a$R$^b$—CR$^a$R$^b$— or —CR$^a$R$^b$—CR$^a$R$^b$—CR$^a$R$^b$—, particularly —CH—CHCH$_3$—, —CHCH$_3$—CH$_2$—, —CH$_2$—CH$_2$— or —CH$_2$—CH$_2$—CH$_2$—.

In a particular embodiment of the invention, —X—Y— is —O—(CR$^a$R$^b$)$_n$—, —S—CR$^a$R$^b$—, —N(R$^a$)CR$^a$R$^b$—, —CR$^a$R$^b$—CR$^a$R$^b$—, —O—CR$^a$R$^b$—O—CR$^a$R$^b$—, —CR$^a$R$^b$—O—CR$^a$R$^b$—, —C(=CR$^a$R$^b$)—CR$^a$R$^b$—, —N(R$^a$)CR$^a$R$^b$—, —O—N(R$^a$)—CR$^a$R$^b$— or —N(R$^a$)—O—CR$^a$R$^b$—.

In a particular embodiment of the invention, R$^a$ and R$^b$ are independently selected from the group consisting of hydrogen, halogen, hydroxyl, alkyl and alkoxyalkyl, in particular hydrogen, halogen, alkyl and alkoxyalkyl.

In another embodiment of the invention, R$^a$ and R$^b$ are independently selected from the group consisting of hydrogen, fluoro, hydroxyl, methyl and —CH$_2$—O—CH$_3$, in particular hydrogen, fluoro, methyl and —CH$_2$—O—CH$_3$.

Advantageously, one of R$^a$ and R$^b$ of —X—Y— is as defined above and the other ones are all hydrogen at the same time.

In a further particular embodiment of the invention, R$^a$ is hydrogen or alkyl, in particular hydrogen or methyl.

In another particular embodiment of the invention, R$^b$ is hydrogen or alkyl, in particular hydrogen or methyl.

In a particular embodiment of the invention, one or both of R$^a$ and R$^b$ are hydrogen.

In a particular embodiment of the invention, only one of R$^a$ and R$^b$ is hydrogen.

In one particular embodiment of the invention, one of R$^a$ and R$^b$ is methyl and the other one is hydrogen.

In a particular embodiment of the invention. R$^a$ and R$^b$ are both methyl at the same time.

In a particular embodiment of the invention, —X—Y— is —O—CH$_2$—, —S—CH$_2$—, —S—CH(CH)—, —NH—CH$_2$—, —O—CH$_2$CH$_2$—, —O—CH(CH$_2$—O—CH$_3$)—, —O—CH(CH$_2$CH$_3$)—, —O—CH(CH$_3$)—, —O—CH$_2$—O—CH$_2$—, —O—CH$_2$—O—CH$_2$—, —CH$_2$—O—CH$_2$—, —C(=CH$_2$)CH$_2$—, —C(=CH$_2$)CH(CH$_3$)—, —N(OCH$_3$)CH$_2$— or —N(CH$_3$)CH$_2$—;

In a particular embodiment of the invention, —X—Y— is —O—CR$^a$R$^b$— wherein R$^a$ and R$^b$ are independently selected from the group consisting of hydrogen, alkyl and alkoxyalkyl, in particular hydrogen, methyl and —CH$_2$—O—CH$_3$.

In a particular embodiment, —X—Y— is —O—CH$_2$— or —O—CH(CH$_3$)—, particularly —O—CH$_2$—

The 2'-4' bridge may be positioned either below the plane of the ribose ring (beta-D-configuration), or above the plane of the ring (alpha-L-configuration), as illustrated in formula (A) and formula (B) respectively.

The LNA nucleoside according to the invention is in particular of formula (B1) or (B2)

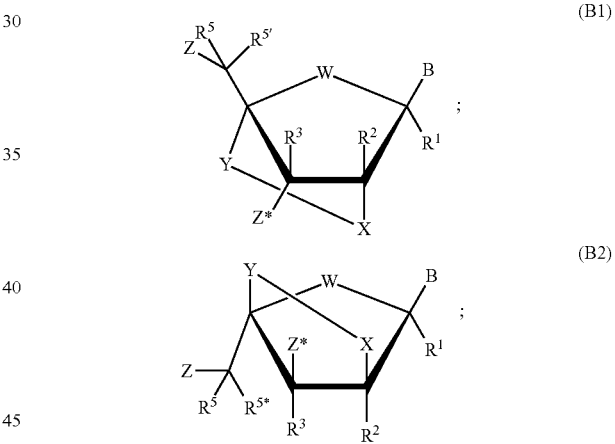

wherein

W is oxygen, sulfur, —N(R$^a$)— or —CR$^a$R$^b$—, in particular oxygen;

B is a nucleobase or a modified nucleobase;

Z is an internucleoside linkage to an adjacent nucleoside or a 5'-terminal group;

Z* is an internucleoside linkage to an adjacent nucleoside or a 3'-terminal group;

R$^1$, R$^2$, R$^3$, R$^5$ and R$^{5*}$ are independently selected from hydrogen, halogen, alkyl, haloalkyl, alkenyl, alkynyl, hydroxy, alkoxy, alkoxyalkyl, azido, alkenyloxy, carboxyl, alkoxycarbonyl, alkylcarbonyl, formyl and aryl; and X, Y, R$^a$ and R$^b$ are as defined above.

In a particular embodiment, in the definition of —X—Y—. R$^a$ is hydrogen or alkyl, in particular hydrogen or methyl. In another particular embodiment, in the definition of —X—Y—R$^b$ is hydrogen or alkyl, in particular hydrogen or methyl. In a further particular embodiment, in the definition of —X—Y—, one or both of R$^a$ and R$^b$ are hydrogen.

In a particular embodiment, in the definition of —X—Y—, only one of $R^a$ and $R^b$ is hydrogen. In one particular embodiment, in the definition of —X—Y—, one of $R^a$ and $R^b$ is methyl and the other one is hydrogen. In a particular embodiment, in the definition of —X—Y—, $R^a$ and $R^b$ are both methyl at the same time.

In a further particular embodiment, in the definition of X, $R^a$ is hydrogen or alkyl, in particular hydrogen or methyl. In another particular embodiment, in the definition of X, $R^b$ is hydrogen or alkyl, in particular hydrogen or methyl. In a particular embodiment, in the definition of X, one or both of $R^a$ and $R^b$ are hydrogen. In a particular embodiment, in the definition of X, only one of $R^a$ and $R^b$ is hydrogen. In one particular embodiment, in the definition of X, one of $R^a$ and $R^b$ is methyl and the other one is hydrogen. In a particular embodiment, in the definition of X, $R^a$ and $R^b$ are both methyl at the same time.

In a further particular embodiment, in the definition of Y, $R^a$ is hydrogen or alkyl, in particular hydrogen or methyl. In another particular embodiment, in the definition of Y, $R^b$ is hydrogen or alkyl, in particular hydrogen or methyl. In a particular embodiment, in the definition of Y, one or both of $R^a$ and $R^b$ are hydrogen. In a particular embodiment, in the definition of Y, only one of $R^a$ and $R^b$ is hydrogen. In one particular embodiment, in the definition of Y, one of $R^a$ and $R^b$ is methyl and the other one is hydrogen. In a particular embodiment, in the definition of Y, $R^a$ and $R^b$ are both methyl at the same time.

In a particular embodiment of the invention $R^1$, $R^2$, $R^3$, $R^5$ and $R^{5*}$ are independently selected from hydrogen and alkyl, in particular hydrogen and methyl.

In a further particular advantageous embodiment of the invention, $R^1$, $R^2$, $R^3$, $R^5$ and $R^{5*}$ are all hydrogen at the same time.

In another particular embodiment of the invention, $R^1$, $R^2$, $R^3$, are all hydrogen at the same time, one of $R^5$ and $R^{5*}$ is hydrogen and the other one is as defined above, in particular alkyl, more particularly methyl.

In a particular embodiment of the invention, $R^5$ and $R^{5*}$ are independently selected from hydrogen, halogen, alkyl, alkoxyalkyl and azido, in particular from hydrogen, fluoro, methyl, methoxyethyl and azido. In particular advantageous embodiments of the invention, one of $R^5$ and $R^{5*}$ is hydrogen and the other one is alkyl, in particular methyl, halogen, in particular fluoro, alkoxyalkyl, in particular methoxyethyl or azido; or $R^5$ and $R^{5*}$ are both hydrogen or halogen at the same time, in particular both hydrogen of fluoro at the same time. In such particular embodiments, W can advantageously be oxygen, and —X—Y— advantageously —O—CH$_2$—.

In a particular embodiment of the invention, —X—Y— is —O—CH$_2$—, W is oxygen and $R^1$, $R^2$, $R^3$, $R^5$ and $R^{5*}$ are all hydrogen at the same time. Such LNA nucleosides are disclosed in WO 99/014226, WO 00/66604, WO 98/039352 and WO 2004/046160, which are all hereby incorporated by reference, and include what are commonly known in the art as beta-D-oxy LNA and alpha-L-oxy LNA nucleosides.

In another particular embodiment of the invention, —X—Y— is —S—CH$_2$—, W is oxygen and $R^1$, $R^2$, $R^3$, $R^5$ and $R^{5*}$ are all hydrogen at the same time. Such thio LNA nucleosides are disclosed in WO 99/014226 and WO 2004/046160, which are hereby incorporated by reference.

In another particular embodiment of the invention, —X—Y— is —NH—CH$_2$—, W is oxygen and $R^1$, $R^2$, $R^3$, $R^5$ and $R^{5*}$ are all hydrogen at the same time. Such amino LNA nucleosides are disclosed in WO 99/014226 and WO 2004/046160, which are hereby incorporated by reference.

In another particular embodiment of the invention, —X—Y— is —O—CH$_2$CH$_2$— or —OCH$_2$CH$_2$CH$_2$—, W is oxygen, and $R^1$, $R^2$, $R^3$, $R^5$ and $R^{5*}$ are all hydrogen at the same time.

Such LNA nucleosides are disclosed in WO 00/047599 and Morita et al., Bioorganic & Med. Chem. Lett. 12, 73-76, which are hereby incorporated by reference, and include what are commonly known in the art as 2'-O-4'C-ethylene bridged nucleic acids (ENA).

In another particular embodiment of the invention, —X—Y— is —O—CH$_2$—, W is oxygen, $R^1$, $R^2$, $R^3$ are all hydrogen at the same time, one of $R^5$ and $R^{5*}$ is hydrogen and the other one is not hydrogen, such as alkyl, for example methyl. Such 5' substituted LNA nucleosides are disclosed in WO 2007/134181, which is hereby incorporated by reference.

In another particular embodiment of the invention, —X—Y— is —O—CR$^a$R$^b$—, wherein one or both of $R^a$ and $R^b$ are not hydrogen, in particular alkyl such as methyl, W is oxygen, $R^1$, $R^2$, $R^3$ are all hydrogen at the same time, one of $R^5$ and $R^{5*}$ is hydrogen and the other one is not hydrogen, in particular alkyl, for example methyl. Such bis modified LNA nucleosides are disclosed in WO 2010/077578, which is hereby incorporated by reference.

In another particular embodiment of the invention, —X—Y— is —O—CHR$^a$—, W is oxygen and $R^1$, $R^2$, $R^3$, $R^5$ and $R^{5*}$ are all hydrogen at the same time. Such 6'-substituted LNA nucleosides are disclosed in WO 2010/036698 and WO 2007/090071, which are both hereby incorporated by reference. In such 6'-substituted LNA nucleosides. $R^a$ is in particular $C_1$-$C_6$ alkyl, such as methyl.

In another particular embodiment of the invention, —X—Y— is —O—CH(CH$_2$—O—CH$_3$)— ("2' O-methoxyethyl bicyclic nucleic acid", Seth et al. J. Org. Chem. 2010, Vol 75(5) pp. 1569-81).

In another particular embodiment of the invention, —X—Y— is —O—CH(CH$_2$CH$_3$)—;

In another particular embodiment of the invention, —X—Y— is —O—CH(CH$_2$—O—CH$_3$)—, W is oxygen and $R^1$, $R^2$, $R^3$, $R^5$ and $R^{5*}$ are all hydrogen at the same time. Such LNA nucleosides are also known in the art as cyclic MOEs (cMOE) and are disclosed in WO 2007/090071.

In another particular embodiment of the invention, —X—Y— is —O—CH(CH$_3$)— ("2'O-ethyl bicyclic nucleic acid". Seth at al., J. Org. Chem. 2010, Vol 75(5) pp. 1569-81).

In another particular embodiment of the invention, —X—Y— is —O—CH$_2$—O—CH$_2$— (Seth et al., J. Org. Chem 2010 op. cit.) In another particular embodiment of the invention, —X—Y— is —O—CH(CH$_3$)—, W is oxygen and $R^1$, $R^2$, $R^3$, $R^5$ and $R^{5*}$ are all hydrogen at the same time. Such 6'-methyl LNA nucleosides are also known in the art as cET nucleosides, and may be either (S)-cET or (R)-cET diastereoisomers, as disclosed in WO 2007/090071 (beta-D) and WO 2010/036698 (alpha-L) which are both hereby incorporated by reference.

In another particular embodiment of the invention, —X—Y— is —O—CR$^a$R$^b$—, wherein neither $R^a$ nor $R^b$ is hydrogen, W is oxygen and $R^1$, $R^2$, $R^3$, $R^5$ and $R^{5*}$ are all hydrogen at the same time. In a particular embodiment, $R^a$ and $R^b$ are both alkyl at the same time, in particular both methyl at the same time. Such 6'-di-substituted LNA nucleosides are disclosed in WO 2009/006478, which is hereby incorporated by reference.

In another particular embodiment of the invention, —X—Y— is —S—CHR$^a$—, W is oxygen and $R^1$, $R^2$, $R^3$, $R^5$ and $R^{5*}$ are all hydrogen at the same time. Such 6'-substituted thio LNA nucleosides are disclosed in WO 2011/156202, which is hereby incorporated by reference. In a particular embodiment of such 6′-substituted thio LNA, $R^a$ is alkyl, in particular methyl.

In a particular embodiment of the invention, —X—Y— is —C(=CH$_2$)C(R$^a$R$^b$)—, —C(=CHF)C(R$^a$R$^b$)— or —C(=CF$_2$)C(R$^a$R$^b$)—, W is oxygen and $R^1$, $R^2$, $R^3$, $R^5$ and $R^{5*}$ are all hydrogen at the same time. $R^a$ and $R^b$ are advantageously independently selected from hydrogen, halogen, alkyl and alkoxyalkyl, in particular hydrogen, methyl, fluoro and methoxymethyl. $R^a$ and $R^b$ are in particular both hydrogen or methyl at the same time or one of $R^a$ and $R^b$ is hydrogen and the other one is methyl. Such vinyl carbo LNA nucleosides are disclosed in WO 2008/154401 and WO 2009/067647, which are both hereby incorporated by reference.

In a particular embodiment of the invention, —X—Y— is —N(OR$^a$)—CH$_2$—, W is oxygen and $R^1$, $R^2$, $R^3$, $R^5$ and $R^{5*}$ are all hydrogen at the same time. In a particular embodiment, $R^a$ is alkyl such as methyl. Such LNA nucleosides are also known as N substituted LNAs and are disclosed in WO 2008/150729, which is hereby incorporated by reference.

In a particular embodiment of the invention, —X—Y— is —O—N(R$^a$)—, —N(R$^a$)—O—, —NR$^a$—CR$^a$R$^b$— CR$^a$R$^b$— or —NR$^a$—CR$^a$R$^b$—, W is oxygen and $R^1$, $R^2$, $R^3$, $R^5$ and $R^{5*}$ are all hydrogen at the same time. $R^a$ and $R^b$ are advantageously independently selected from hydrogen, halogen, alkyl and alkoxyalkyl, in particular hydrogen, methyl, fluoro and methoxymethyl.

In a particular embodiment, $R^a$ is alkyl, such as methyl, $R^b$ is hydrogen or methyl, in particular hydrogen. (Seth et al., J. Org. Chem 2010 op. cit.).

In a particular embodiment of the invention, —X—Y— is —O—N(CH)— (Seth et al., J. Org. Chem 2010 op. cit.).

In a particular embodiment of the invention, $R^5$ and $R^{5*}$ are both hydrogen at the same time. In another particular embodiment of the invention, one of $R^5$ and $R^{5*}$ is hydrogen and the other one is alkyl, such as methyl. In such embodiments, $R^1$, $R^2$ and $R^3$ can be in particular hydrogen and —X—Y— can be in particular —O—CH$_2$— or —O—CHC (R$^a$)$_3$—, such as —O—CH(CH$_3$)—.

In a particular embodiment of the invention, —X—Y— is —CR$^a$R$^b$—O—CR$^a$R$^b$—, such as —CH$_2$—O—CH$_2$—, W is oxygen and $R^1$, $R^2$, $R^3$, $R^5$ and $R^{5*}$ are all hydrogen at the same time. In such particular embodiments, $R^a$ can be in particular alkyl such as methyl, $R^b$ hydrogen or methyl, in particular hydrogen. Such LNA nucleosides are also known as conformationally restricted nucleotides (CRNs) and are disclosed in WO 2013/036868, which is hereby incorporated by reference.

In a particular embodiment of the invention, —X—Y— is —O—CR$^a$R$^b$—O—CR$^a$R$^b$—, such as —O—CH$_2$—O— CH$_2$—, W is oxygen and $R^1$, $R^2$, $R^3$, $R^5$ and $R^{5*}$ are all hydrogen at the same time. $R^a$ and $R^b$ are advantageously independently selected from hydrogen, halogen, alkyl and alkoxyalkyl, in particular hydrogen, methyl, fluoro and methoxymethyl. In such a particular embodiment, $R^a$ can be in particular alkyl such as methyl. $R^b$ hydrogen or methyl, in particular hydrogen. Such LNA nucleosides are also known as COC nucleotides and are disclosed in Mitsuoka et al., Nucleic Acids Research 2009, 37(4), 1225-1238, which is hereby incorporated by reference.

It will be recognized than, unless specified, the LNA nucleosides may be in the beta-D or alpha-L stereoisoform.

Particular examples of LNA nucleosides of the invention are presented in Scheme 1 (wherein B is as defined above).

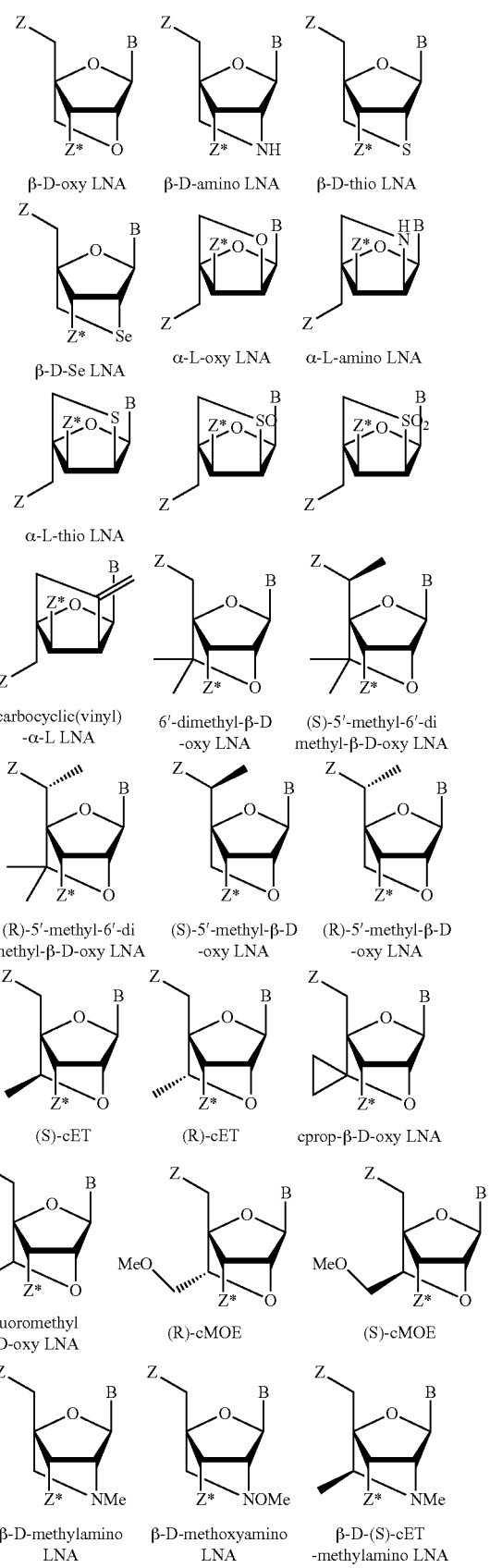

Scheme 1

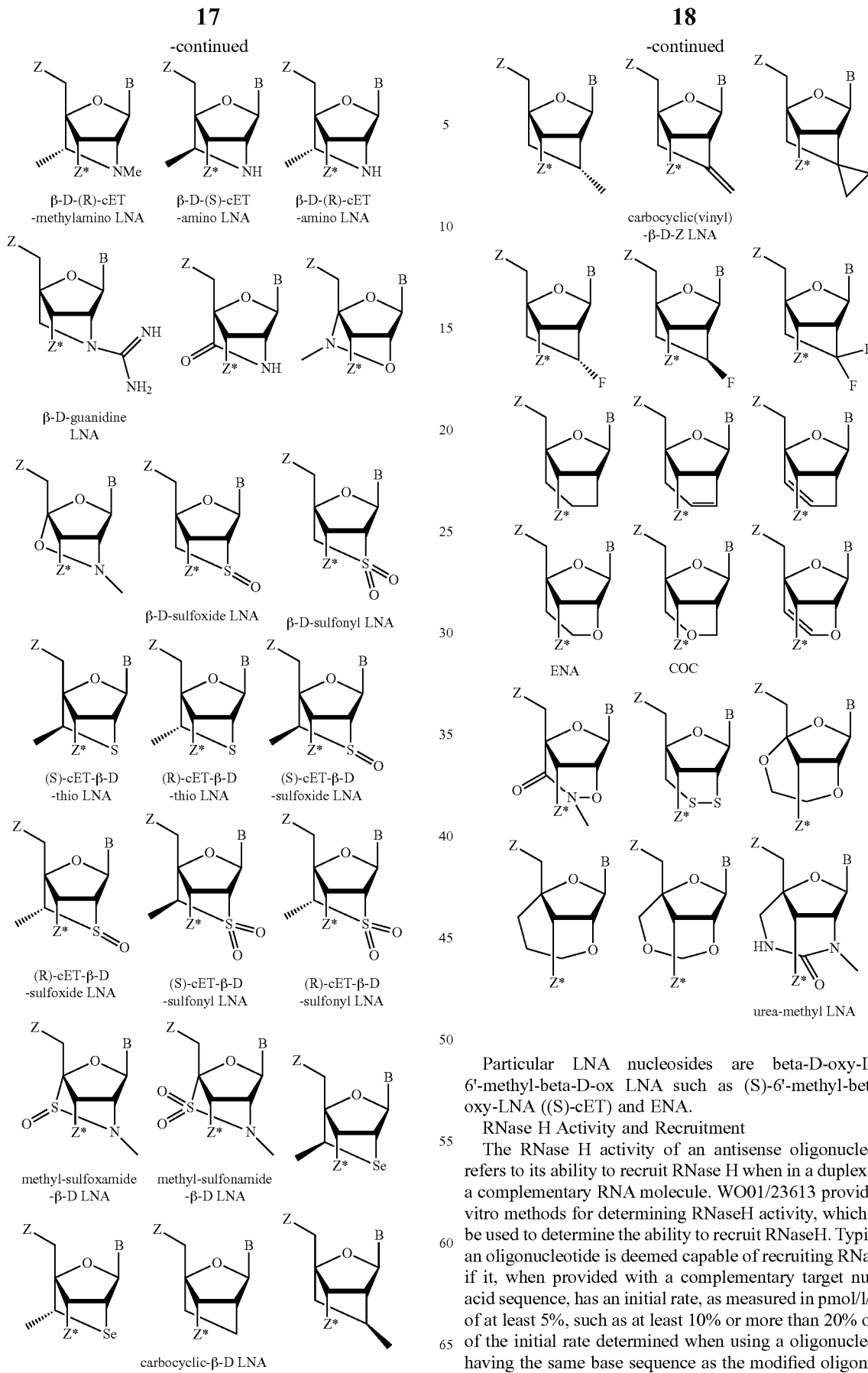

Particular LNA nucleosides are beta-D-oxy-LNA, 6'-methyl-beta-D-ox LNA such as (S)-6'-methyl-beta-D-oxy-LNA ((S)-cET) and ENA.

RNase H Activity and Recruitment

The RNase H activity of an antisense oligonucleotide refers to its ability to recruit RNase H when in a duplex with a complementary RNA molecule. WO01/23613 provides in vitro methods for determining RNaseH activity, which may be used to determine the ability to recruit RNaseH. Typically an oligonucleotide is deemed capable of recruiting RNase H if it, when provided with a complementary target nucleic acid sequence, has an initial rate, as measured in pmol/l/min, of at least 5%, such as at least 10% or more than 20% of the of the initial rate determined when using a oligonucleotide having the same base sequence as the modified oligonucleotide being tested, but containing only DNA monomers with phosphorothioate linkages between all monomers in the oligonucleotide, and using the methodology provided by Example 91-95 of WO01/23613 (hereby incorporated by reference). For use in determining RHase H activity, recombinant human RNase H1 is available from Lubio Science GmbH. Lucerne. Switzerland.

Nucleoside Immobilized on a Solid Support

The conventional chemical nomenclature for nucleosides is as depicted below. In the expression "nucleoside immobilized on a solid support", the nucleoside is generally linked to the solid support via its 3' position.

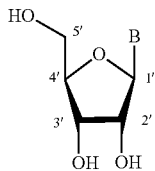

It is to be understood that the above representation solely serves the purpose of illustration at what position the nucleoside can be attached to the solid support. Many different nucleosides fall under this expression, including modified nucleosides such as sugar-modified nucleosides and nucleosides with a hydroxyl protected moiety as described herein.

Suitable solid supports for oligonucleotide synthesis are known in the art. Examples of such solid supports are to be found in numerous papers, such as in Solid-Phase Supports for Oligonucleotide Synthesis Current Protocols in Nucleic Acid Chemistry (2000) 3.1.1-3.1.28.

Attached to the Oxygen Atom of Formula 1a or 1b Via its 3' Position

The conventional chemical nomenclature for nucleosides is as depicted below. In the expression "attached to the oxygen atom of Formula 1a or 1b via its 3' position", the 3' position it is referred to is depicted below.

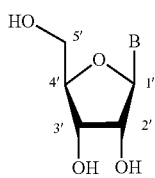

Non limiting illustrations of how the attachment is made to Formula 1a or 1b are given herein, for examples with Formula 4a, 4b, 5a, 5b, 6a, 6b, 7a, 7b, 8a, 8b, 8c, 8d, 9a, 9b, 9c, 9d etc.

It is to be understood that the above representation solely serves the purpose of illustration at what position the nucleoside can be attached to the monomer of Formula 1a or 1b. Many different nucleosides fall under this expression, including modified nucleosides such as sugar-modified nucleosides and nucleosides with a hydroxyl protected moiety as described herein.

Oxazaphospholidines

The method of the invention comprises the step of coupling an oxazaphospholidine to a nucleoside or nucleotide. The stereocenter is in the L position, as illustrated in formula 1a. In some embodiments, the stereocenter is in the D position, as illustrated in formula 1b:

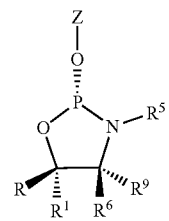

Formula 1a

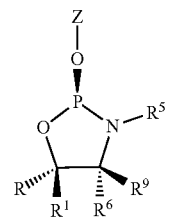

Formula 1b

The monomer comprising the stereocenter created by the R and $R^1$ groups as shown in formula 1a is referred to as an L monomer herein, which results in the formation of a Sp stereocenter. The monomer comprising the stereocenter created by the R and $R^1$ groups as shown in formula 1b is referred to as a D monomer herein, which results in the formation of an Rp stereocenter.

When substituted, R may be substituted with a group selected from the group consisting of: $C_{1-4}$ alkyl, $C_{6-14}$ aryl group, $C_{1-4}$ alkoxy, $C_{6-14}$ aryl group, or $C_{6-14}$ aryl $C_{1-4}$ alkyl group. Multiple substitutions may be dependently or independently selected from the group consisting of: $C_{1-4}$ alkyl group, $C_{6-14}$ aryl group $C_{1-4}$, alkoxy group, $C_{7-14}$ aralkyl group, $C_{1-4}$ alkyl, $C_{6-14}$ aryl group, $C_{1-4}$ alkoxy, $C_{6-14}$ aryl group, or $C_{6-14}$ aryl $C_{1-4}$ alkyl group.

When substituted, R may be substituted with a group selected from the group consisting of: silyl substituted by one or more $C_{1-4}$-alkyl and/or $C_{6-14}$ aryl, $C_{1-4}$ alkyl, $C_{6-14}$ aryl and $C_{1-4}$, alkoxy.

In some embodiments R is selected from the groups consisting of aryl, heteroaryl, substituted aryl, substituted heteroaryl, nitro, halogen, cyano, silyl, substituted silyl, sulfone, substituted sulfone (aryl substituted sulfone), fluorene, and substituted fluorene.

In some embodiments, R is silyl substituted by one or more $C_{1-4}$-alkyl and/or $C_{6-14}$ aryl, in particular —Si(Ph)$_2$Me.

In some embodiments, R is selected from the group consisting of aryl, heteroaryl, substituted aryl and substituted heteroaryl.

In some embodiments, R is aryl, such as phenyl.

In some embodiments, when R is substituted aryl, R may be substituted with halide, such as iodide, fluoride, bromide or chloride, such as phenyl substituted with halide, such as iodide, fluoride, bromide or chloride.

In some embodiments. $R^1$ is hydrogen. In some embodiments $R^1$ is $C_{1-3}$ alkyl, such as methyl, ethyl or propyl. In some embodiments $R^1$ is methyl.

In some embodiments, R is aryl, such as phenyl and $R^1$ is hydrogen.

In some embodiments, R is silyl substituted by one or more $C_{1-4}$-alkyl and/or $C_{6-14}$ aryl, such as —Si(Ph)$_2$Me and $R^1$ is hydrogen.

In some embodiments, R is aryl, such as phenyl, and $R^1$ is $C_{1-3}$ alkyl, such as methyl, ethyl or propyl.

In some embodiments R is:

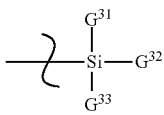

wherein $G^{31}$, $G^{32}$ and $G^{33}$ are independently selected from the groups consisting of $C_{1-4}$ alkyl, $C_{6-14}$ aryl$C_{1-4}$ alkoxy, $C_{7-14}$ aralkyl, $C_{1-4}$ alkyl$C_{6-14}$ aryl. $C_{1-4}$ alkoxy$C_{6-14}$ aryl, and $C_{6-14}$ aryl$C_{1-4}$ alkyl.

In some embodiments R is

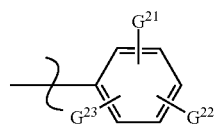

wherein $G^{21}$, $G^{22}$ and $G^{23}$ are independently hydrogen, nitro, halogen, cyano or $C_{1-3}$ alkyl.

In some embodiments R is

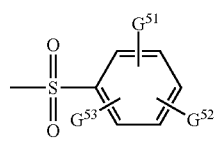

wherein $G^{51}$, $G^{52}$ and $G^{53}$ are independently hydrogen, nitro, halogen, cyano or $C_{1-3}$ alkyl or $C_{1-3}$ alkyloxy group.

In some embodiments $R^5$ and $R^6$ together form a heterocylic ring (with the cyclic nitrogen shown in Formula 1)—nucleoside monomers referred to as bicyclic oxazaphospholidines. The heterocyclic ring may comprise, for example 3-16 carbon atoms, such as 4 carbons atoms.

Orthogonally Protected Oxazaphospholidine Monomers

EP17163506.3, hereby incorporated by reference, provides oxazaphospholidine monomers comprising orthogonally protected amine groups on the oxazaphospholidine chiral auxiliary. In some embodiments the oxazaphospholidine monomer is an orthogonally protected oxazaphospholidine monomer.

Bicyclic Oxazaphospholidine Monomers

In some embodiments the monomer is a bicyclic oxazaphospholidine monomer, e.g. in some embodiments $R^5$ and $R^6$ together form a heterocylic ring. In some embodiments $R^5$ and $R^6$ together form a heterocylic ring (with the cyclic nitrogen shown in Formula 1) which comprises 4 carbon atoms, making a total of five atoms in the heterocyclic ring (4 carbon and the nitrogen shown in Formula 1). For example, the oxazaphospholidine used according to the invention may be of formula 2a or 2b:

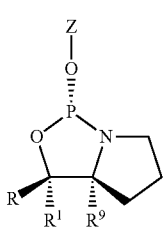

Formula 2a

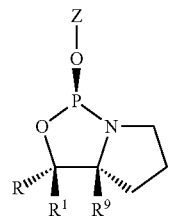

Formula 2b

Wherein R, $R^1$, $R^9$ and Z are as according to formula 1.

In some embodiments $R^5$ and $R^6$ together form a heterocylic ring (with the cyclic nitrogen shown in Formula I) which comprises 4 carbon atoms, making a total of five atoms in the heterocyclic ring (4 carbon and the nitrogen shown in Formula 1), and R is aryl, such as phenyl, $R^1$ is hydrogen or methyl. $R^9$ is hydrogen.

The Z group above is a nucleoside where the Y oxygen of the nucleoside is the exocyclic oxygen shown in formula 1, 1a, 1b, 2a or 2b. In some embodiments the Z group is a LNA nucleoside moiety. In some embodiments the Z group is a DNA nucleoside moiety. In some embodiment the oxazaphospholidine monomer used according to the invention may therefore be represented as the compound of formula 3a or 3b:

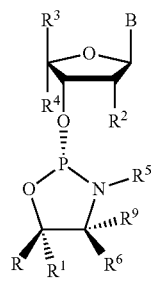

Formula 3a

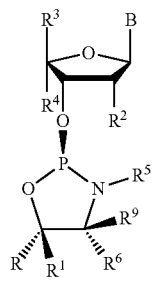

Formula 3b wherein, R, $R^1$, $R^5$, $R^6$ and $R^9$ are as described herein and B is a nucleobase.

DESCRIPTION OF THE FIGURES

FIG. 2 depicts a series of graphs, FIGS. 2A, 2B and 2C, based on an Ultra Performance Liquid Chromatography— mass spectrometry tandem analysis. The graphs exhibit the analysis of the crude material after coupling of a 15-mer fully phosphorothioated DNA T oligonucleotide with a L-DNA T monomer using various coupling activators and solvents to obtain a 16-mer oligonucleotide in a method according to the invention.

Figures 3A, 3B, 3C, 3D:
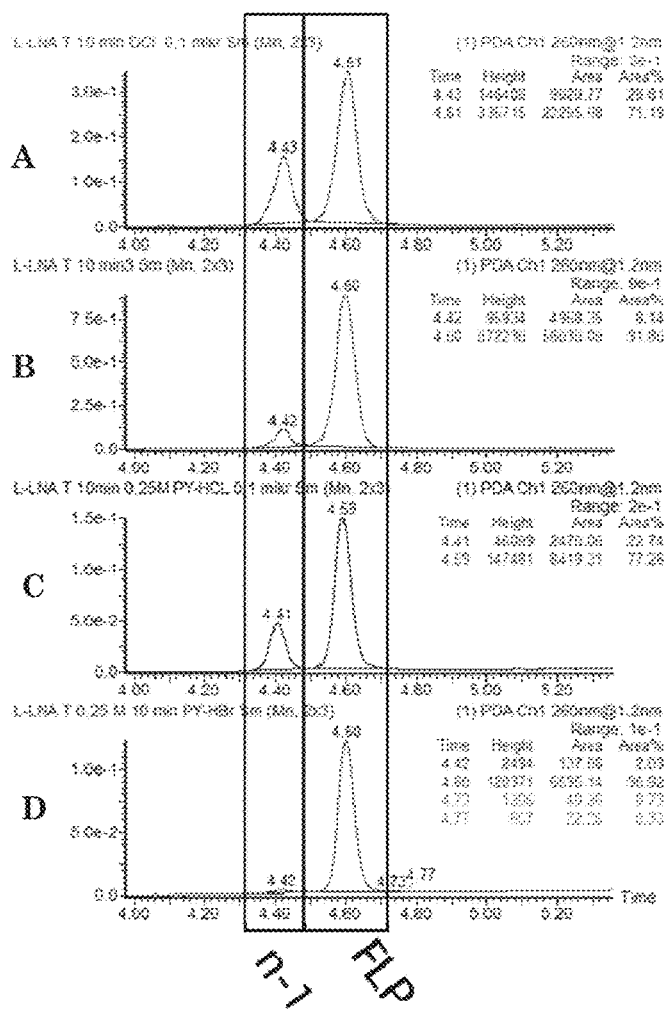

FIG. 3 depicts a series of graphs, FIGS. 3A, 3B, 3C and 3D, based on an Ultra Performance Liquid Chromatography—mass spectrometry tandem analysis. The graphs exhibit the analysis of the crude material after coupling of a 15-mer fully phosphorothioated DNA T oligonucleotide with a L-DNA T monomer using various coupling activators and solvents to obtain a 16-mer oligonucleotide in a method according to the invention.

Figures 4A, 4B, 4C:
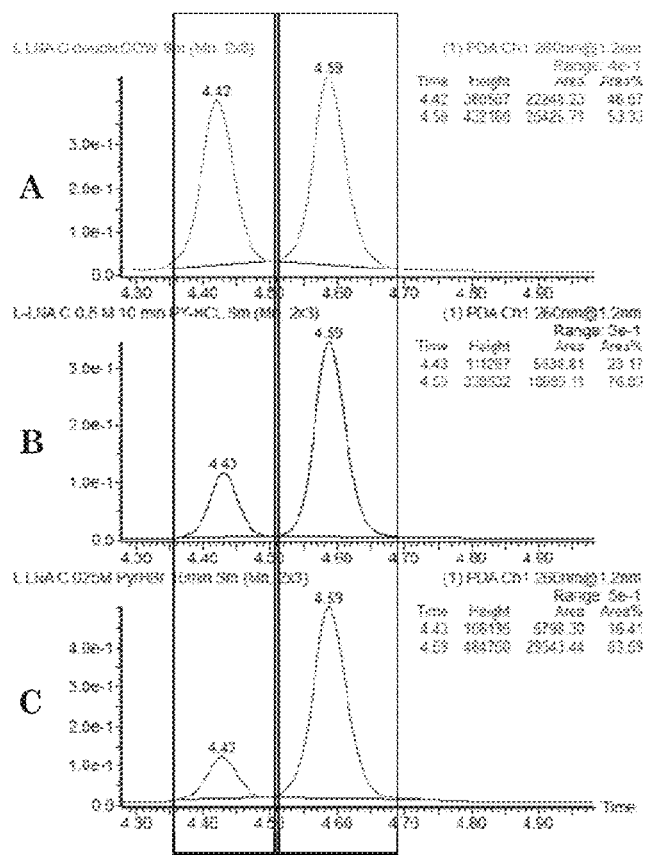

FIG. 4 depicts a series of graphs, FIGS. 4A, 4B and 4C, based on an Ultra Performance Liquid Chromatography—mass spectrometry tandem analysis. The graphs exhibit the analysis of the crude material after coupling of a 15-mer fully phosphorothioated DNA T oligonucleotide with an LNA$^m$C monomer using various coupling activators and solvents to obtain a 16-mer oligonucleotide in a method according to the invention.

FIG. 5 depicts a series of graphs, FIGS. 5A and 5B, based on an Ultra Performance Liquid Chromatography—mass spectrometry tandem analysis. The graphs exhibit the analysis of the crude material after coupling of a 15-mer fully phosphorothioated DNA T oligonucleotide with a LNA$^m$C monomer using various coupling activators and solvents to obtain a 16-mer oligonucleotide in a method according to the invention.

FIG. 6 depicts a series of graphs, FIGS. 6A, 6B, 6C, 6D and 6E, based on an Ultra Performance Liquid Chromatography—mass spectrometry tandem analysis. The graphs exhibit the analysis of the crude material after coupling of a 15-mer fully phosphorothioated DNA T oligonucleotide with a LNA$^m$C monomer using various coupling activators and solvents to obtain a 16-mer oligonucleotide in a method according to the invention.

Figure 7:
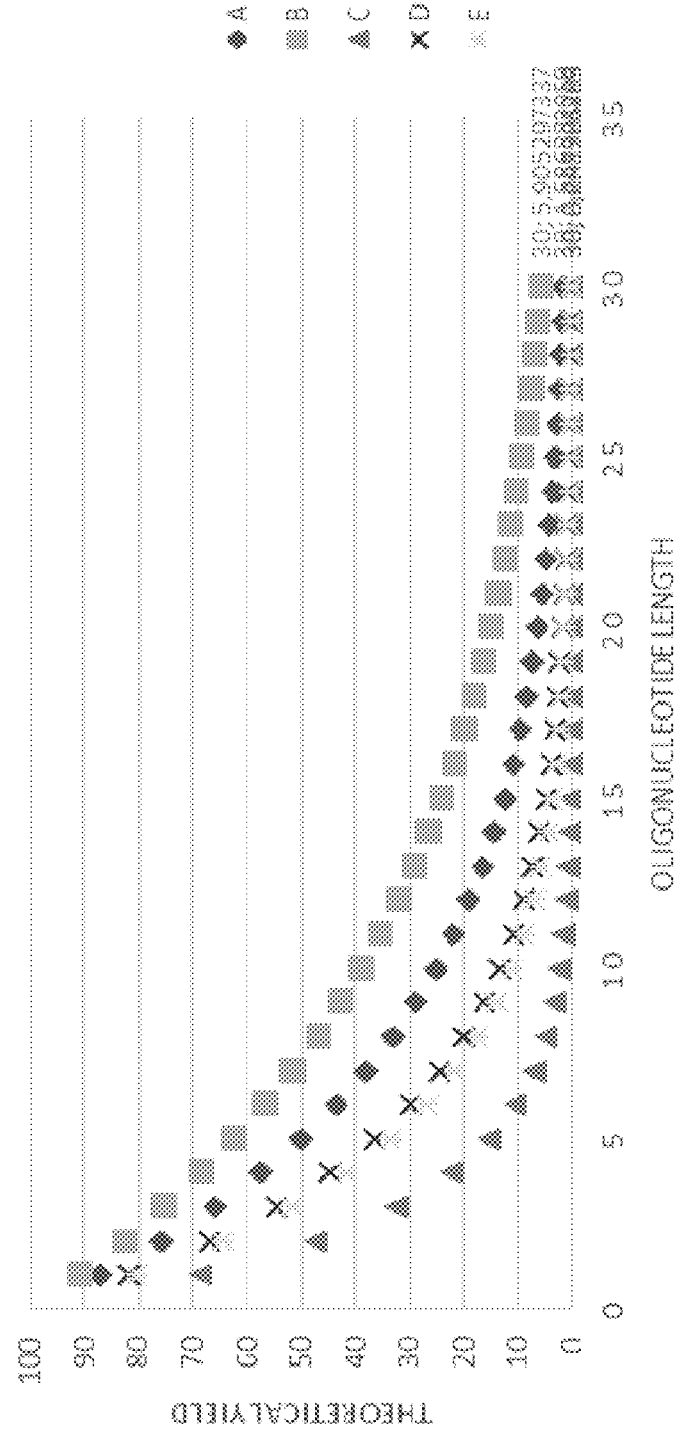

FIG. 7 depicts a graph of the theoretical coupling yields using various activators as per example and FIG. 1.

Figure 8:
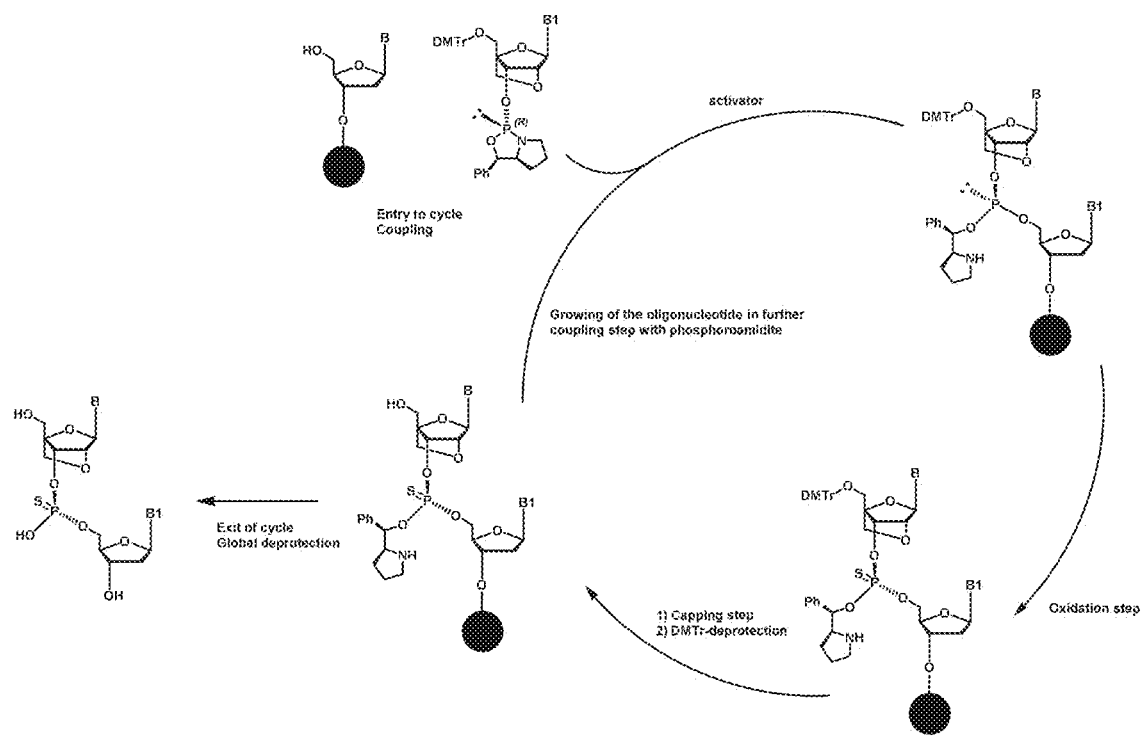

FIG. 8 depicts the synthesis of oligonucleotides with a coupling step according to the present invention.

DETAILED DESCRIPTION OF THE INVENTION

In a first aspect, the invention relates to method for the synthesis of stereodefined, sugar modified oligonucleotides comprising a step of coupling an oxazaphospholidine monomer of formula (1a) or (1b):

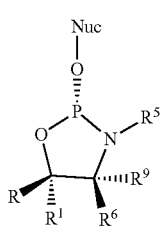

Formula 1a

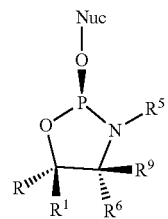

Formula 1b wherein Nuc is a nucleoside comprising a protected 5'-hydroxyl and is attached to the oxygen atom of Formula 1a or 1b via its 3' position;

R is selected from the groups consisting of nitro, halogen, cyano, silyl, sulfone, $C_{1-4}$ alkyl, $C_{1-4}$ alkylsulfone, $C_{6-14}$ arylsulfone, $C_{6-14}$ aryl, $C_{5-14}$ heteroaryl comprising one, two or three heteroatoms independently selected from O, N or S, each of the silyl, alkyl, aryl, heteroaryl moieties can be unsubstituted or substituted by one or more group(s) selected from the group consisting of: $C_{1-4}$ alkyl. $C_{6-14}$ aryl and $C_{1-4}$, alkoxy;

$R^1$ is selected from the groups consisting of hydrogen and $C_{1-4}$ alkyl; and $R^5$, $R^6$ and $R^9$ are independently selected from the group consisting of hydrogen, $C_{1-4}$ alkyl, $C_{5-6}$ cycloalkyl, $C_{6-14}$ aryl, $C_{3-4}$ heteroaryl comprising one, two or three heteroatoms independently selected from O, N or S, each of which alkyl, cycloalkyl, aryl or heteroaryl can be substituted by one, two or three substituents selected from the group consisting of $C_{1-4}$ alkyl, $C_{6-14}$ aryl and $C_{1-4}$, alkoxy alternatively, two of $R^5$, $R^6$ or $R^9$ together form a heterocyclic ring comprising 3-7 carbon atoms, together with the N atom to which $R^5$ is attached wherein said heterocyclic ring can be substituted by one, two or three substituents selected from the group consisting of $C_{1-4}$ alkyl, $C_{6-14}$ aryl and $C_{1-4}$ alkoxy.

with a nucleoside immobilized on a solid support wherein the coupling is performed in the presence of a pyridinium acidic salt coupling activator.

In another aspect, the invention relates to method for the synthesis of stereodefined, sugar modified oligonucleotides comprising a step of coupling an oxazaphospholidine monomer of formula (1a) or (1b):

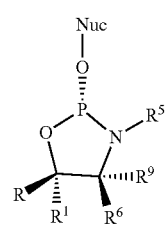

Formula 1a

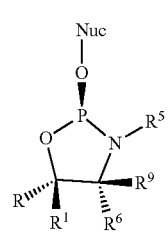

Formula 1b wherein Nuc is a nucleoside comprising a protected 5'-hydroxyl and is attached to the oxygen atom of Formula 1a or 1b via its 3' position;

R is selected from the groups consisting of nitro, halogen, cyano, silyl, sulfone, $C_{1-4}$ alkyl, $C_{1-4}$ alkylsulfone, $C_{6-14}$ arylsulfone, $C_{6-14}$ aryl, $C_{5-14}$ heteroaryl comprising one, two or three heteroatoms independently selected from O, N or S, each of the silyl, alkyl, aryl, heteroaryl moieties can be unsubstituted or substituted by one or more group(s) selected from the group consisting of: silyl substituted by one or more $C_{1-4}$-alkyl and/or $C_{6-14}$ aryl, $C_{1-4}$ alkyl, $C_{6-14}$ aryl and $C_{1-4}$ alkoxy;

$R^1$ is selected from the groups consisting of hydrogen and $C_{1-4}$ alkyl; and $R^5$, $R^6$ and $R^9$ are independently selected from the group consisting of hydrogen, $C_{1-4}$ alkyl, $C_f$ cycloalkyl, $C_{6-14}$ aryl, $C_{3-14}$ heteroaryl comprising one, two or three heteroatoms independently selected from O, N or S, each of which alkyl, cycloalkyl, aryl or heteroaryl can be substituted by one, two or three substituents selected from the group consisting of $C_{1-4}$ alkyl, $C_{6-14}$ aryl and $C_{1-4}$, alkoxy or two of $R^5$, $R^6$ or $R^9$ together form a heterocyclic ring comprising 3-7 carbon atoms, together with the N atom to which $R^5$ is attached wherein said heterocyclic ring can be substituted by one, two or three substituents selected from the group consisting of $C_{1-4}$ alkyl, $C_{6-14}$ aryl and $C_{1-4}$, alkoxy, with a nucleoside immobilized on a solid support wherein the coupling is performed in the presence of a pyridinium acidic salt coupling activator.

In an embodiment of the method according to the invention, the pyridinium acidic salt coupling activator is selected from the group consisting of pyridinium hydrochloride, pyridinium hydrobromide, pyridinium trifluroacetate, pyridinium triflate and pyridinium mesylate.

In an embodiment of the method according to the invention, the pyridinium acidic salt coupling activator is pyridinium triflate at about 0.3, 0.4, 0.5, 0.6, 0.7, 0.8, 0.9, or 1 M.

In an embodiment of the method according to the invention, the pyridinium acidic salt coupling activator is pyridinium triflate at about 0.3 M.

In an embodiment of the method according to the invention, the pyridinium acidic salt coupling activator is pyridinium triflate at about 1 M.

In an embodiment of the method according to the invention the pyridinium acidic salt coupling activator is pyridinium hydrobromide in a range from about 0.05 to about 0.50 M, for example about 0.05, 0.10, 0.15, 0.20, 0.25, 0.30, 0.35, 0.40, 045 or 0.50 M.

In an embodiment of the method according to the invention, the pyridinium acidic salt coupling activator is pyridinium hydrobromide at about 0.25 M.

In an embodiment of the method according to the invention, the pyridinium acidic salt coupling activator is pyridinium hydrochloride in a range from about 0.25 to about 1 M, for example, 0.25, 0.30, 0.35, 0.40, 045, 0.50, 0.55, 0.60, 0.65, 0.70, 0.75, 0.80, 0.85, 0.90, 0.95 or 1 M.

In an embodiment of the method according to the invention, the pyridinium acidic salt coupling activator is pyridinium hydrochloride at about 0.50 M.

In an embodiment of the method according to the invention, the pyridinium acidic salt coupling activator is in a solvent selected from acetonitrile, pyridinium in acetonitrile, methyl imidazole as well as their mixtures.

In an embodiment of the method according to the invention, the pyridinium acid salt coupling activator is in acetonitrile.

In an embodiment of the method according to the invention the method the oxazaphospholidine monomer of formulae (1a) and (1b) are:

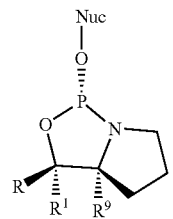

Formula 2a

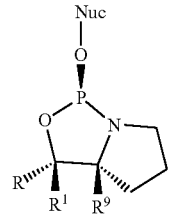

Formula 2b wherein R, $R^1$, $R^9$ and Nuc are defined herein for formula (1a) or (1b).

In an embodiment of the method according to the invention, the sugar modification is selected from the group consisting of the following LNA sugar modifications:

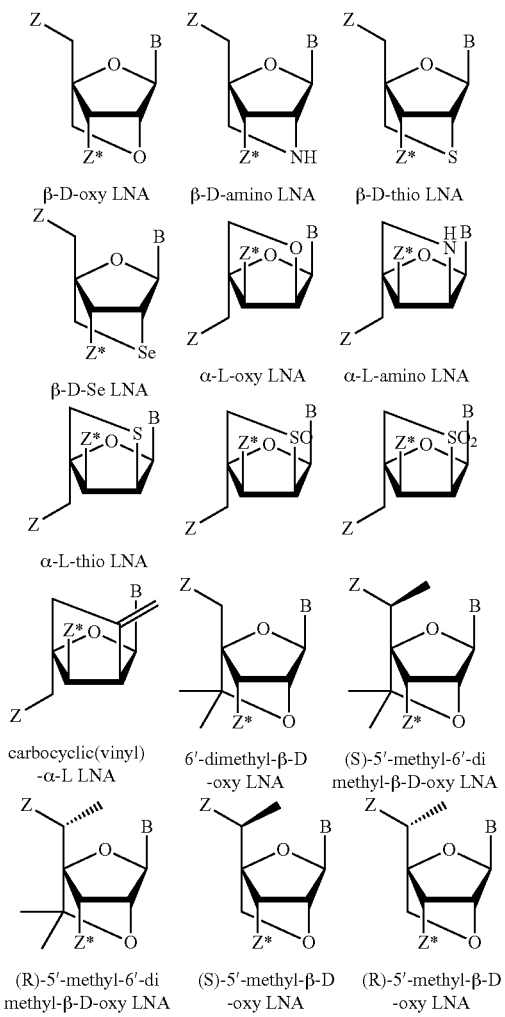

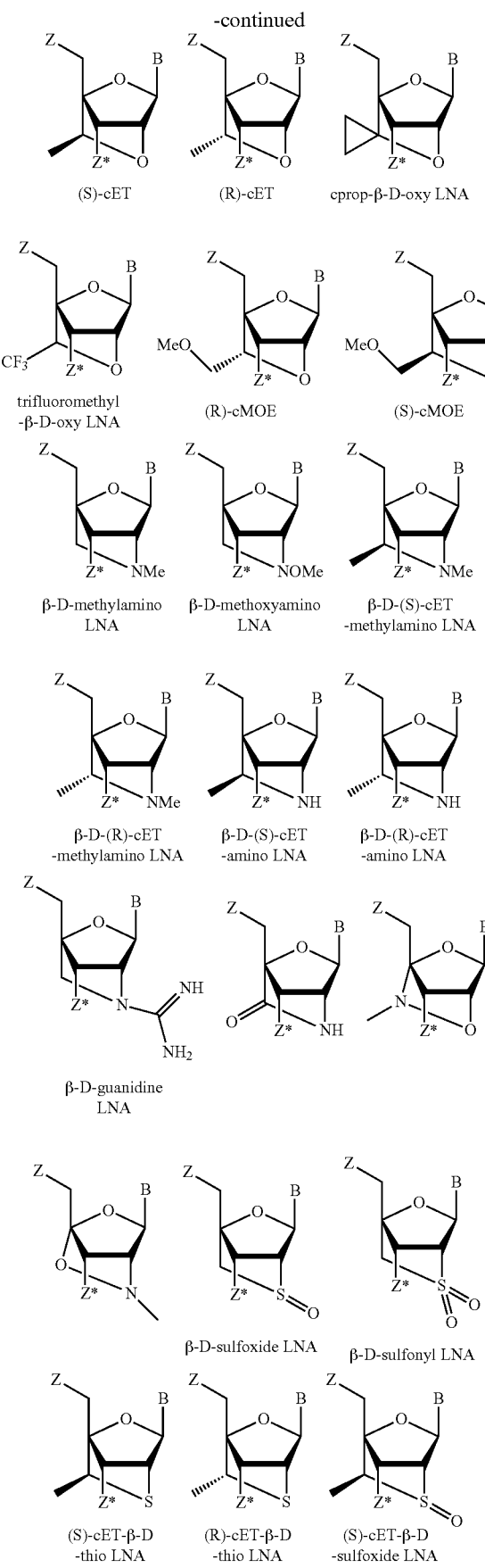
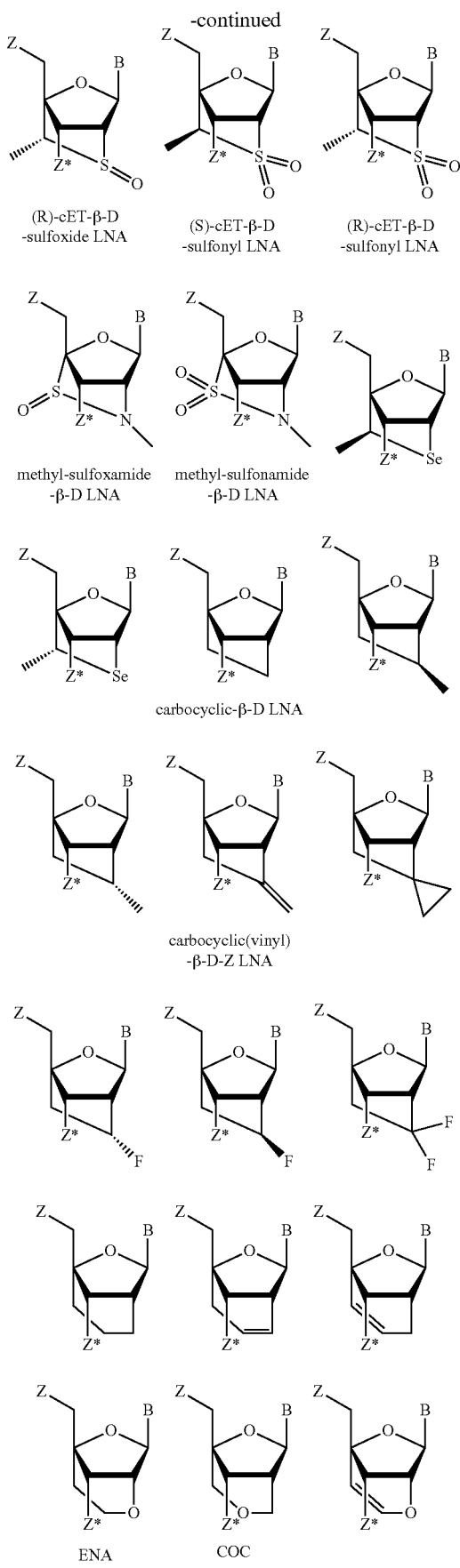

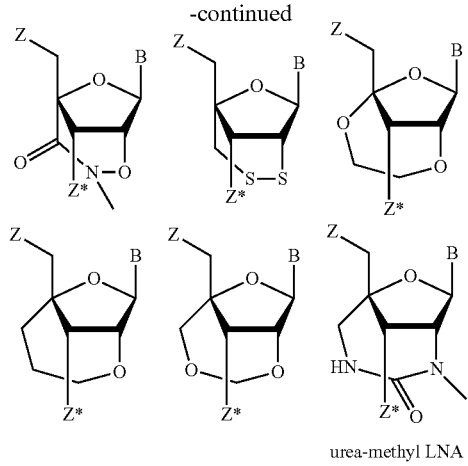

urea-methyl LNA wherein B is a nucleobase and Z and Z* are independently nucleotides.

In an embodiment of the method according to the invention the sugar modification is selected from the group consisting of: beta-D-oxy-LNA, 6'-methyl-beta-D-oxy LNA. (S)-6'-methyl-beta-D-oxy-LNA ((S)-cET) and ENA.

In an embodiment of the method according to the invention, the sugar modification is MOE:

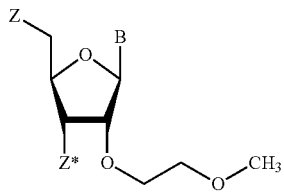

wherein B is a nucleobase and Z and Z* are independently nucleotides.

In each embodiment of the method according to the invention described herein, the oxazaphospholidine monomer can be of formula (3a) or (3b):

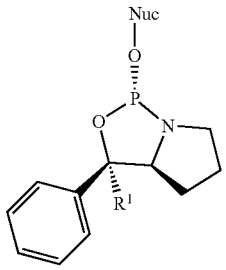

Formula 3a

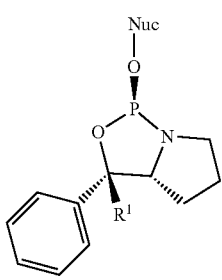

Formula 3b wherein Nuc is as defined herein, R$^1$ is H or methyl.

In an embodiment, the invention is method for the synthesis of stereodefined, oligonucleotides that comprise a ribose modification selected from the group consisting of beta-D-oxy-LNA, 6'-methyl-beta-D-oxy LNA, (S)-6'-methyl-beta-D-oxy-LNA ((S)-cET) and MOE, said method comprising a step of coupling an oxazaphospholidine monomer of formula (3a) or (3b):

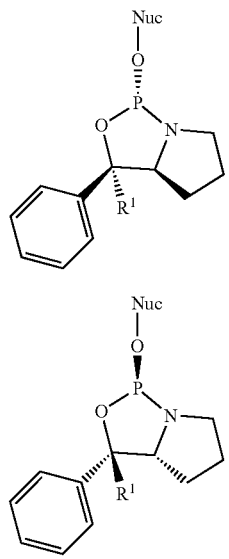

Formula 3a

Formula 3b wherein Nuc is a nucleoside comprising a protected 5'-hydroxyl and is attached to the oxygen atom of Formula 1a or 1b via its 3' position and R$^1$ is selected from the groups consisting of hydrogen and C$_{1-4}$ alkyl; with a nucleoside immobilized on a solid support wherein the coupling is performed in the presence of pyridinium hydrobromide at 0.25 M or pyridinium hydrochloride at 0.50 M as an activator in acetonitrile.

In an embodiment, the invention is method for the synthesis of stereodefined, oligonucleotides that comprise a ribose modification selected from the group consisting of beta-D-oxy-LNA, (S)-6'-methyl-beta-D-oxy-LNA ((S)-cET) and MOE, said method comprising a step of coupling an oxazaphospholidine monomer of formula (3a) or (3b):

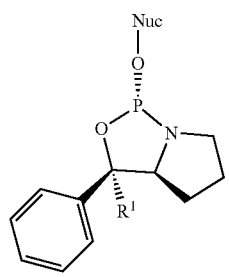

Formula 3a

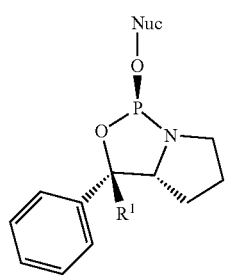

Formula 3b wherein Nuc is a nucleoside comprising a protected 5%-hydroxyl and is attached to the oxygen atom of Formula 1a or 1b via its 3' position and R$^1$ is selected from the groups consisting of hydrogen and C$_{1-4}$ alkyl; with a nucleoside immobilized on a solid support wherein the coupling is performed in the presence of pyridinium hydrobromide at 0.25 M or pyridinium hydrochloride at 0.50 M as an activator in acetonitrile.

In a embodiment, the invention is method for the synthesis of stereodefined, oligonucleotides that comprise a ribose modification selected from the group consisting of beta-D-oxy-LNA, (S)-6'-methyl-beta-D-oxy-LNA ((S)-cET) and MOE, said method comprising a step of coupling an oxazaphospholidine monomer of formula (3a) or (3b):

Formula 3a

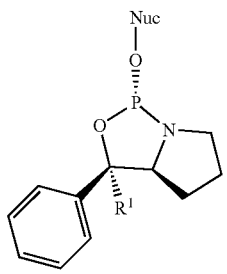

Formula 3b

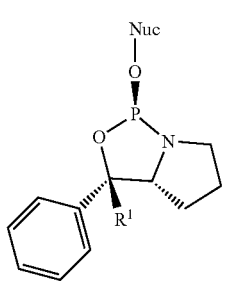

wherein Nuc is a nucleoside comprising a protected 5'-hydroxyl and is attached to the oxygen atom of Formula 1a or 1b via its 3' position and R' is selected from the groups consisting of hydrogen and $C_{1-4}$ alkyl; with a nucleoside immobilized on a solid support wherein the coupling is performed in the presence of pyridinium hydrobromide at 0.25 M as an activator in acetonitrile.

In each embodiment described herein, the oxazaphospholidine monomer can be of formula (4a) or (4b):

Formula 4a

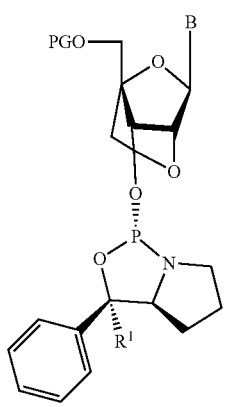

Formula 4b

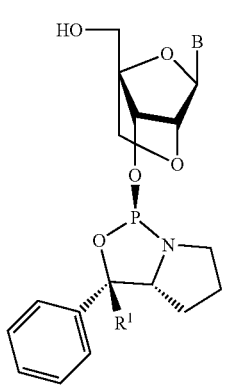

wherein B is a nucleobase, PG is an hydroxyl protecting group and $R^1$ is selected from the groups consisting of hydrogen and $C_{1-4}$ alkyl.

In some or all embodiments, the nucleoside immobilized on a solid support can be of formula (5):

Formula 5

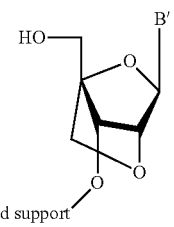

wherein B' is a nucleobase.

In an embodiment, the invention is method for the synthesis of stereodefined, oligonucleotides that comprises the step of coupling an oxazaphospholidine monomer of formula (4a) or (4b):

Formula 4a

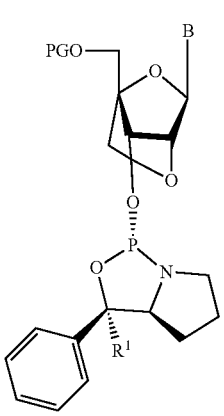

Formula 4b

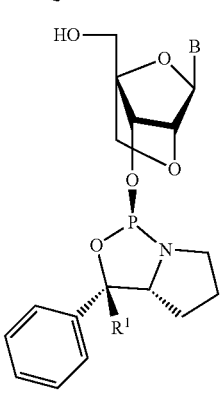

wherein $R^1$ is selected from the groups consisting of hydrogen and $C_{1-4}$ alkyl and B is a nucleobase, with a nucleoside immobilized on a solid support of formula:

Formula 5

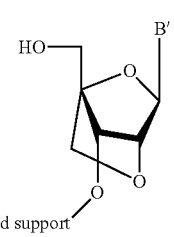

wherein B' is a nucleobase and the coupling is performed in the presence of pyridinium hydrobromide at 0.25 M as an activator in acetonitrile.

Another aspect of the invention is a composition comprising a pyridinium acidic salt activator, a solvent and a oxazaphospholidine of formula (1a) or (1b), wherein the pyridinium acidic salt activator, the solvent and the oxazaphospholidine of formula (1a) or (1b) are as described herein.

In an embodiment, the composition of the invention comprises pyridinium hydrochloride activator at 0.50 M in acetonitrile and an oxazaphospholidine of formula (3a) or (3b):

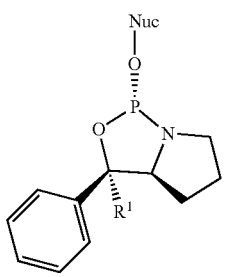

Formula 3a

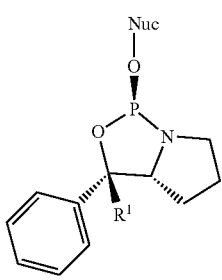

Formula 3b wherein $R^1$ is selected from hydrogen or $C_{1-4}$ alkyl.

In an embodiment, the composition of the invention comprises pyridinium hydrobromide activator at about 0.25 M in acetonitrile and a compound of formula (3a) or (3b):

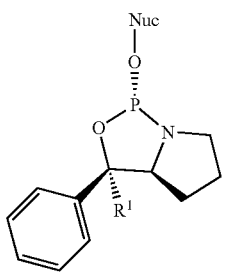

Formula 3a

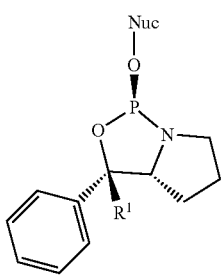

Formula 3b wherein $R^1$ is selected from hydrogen or $C_{1-4}$ alkyl.

Another aspect of the invention is the use of a pyridinium acidic salt activator for the coupling of an oxazaphospholidine monomer of formula (1a) or (1b) as defined herein with a nucleoside immobilized on a solid support.

In an embodiment, a pyridinium hydrochloride activator is used at 0.50 M in acetonitrile for coupling of a nucleoside immobilized on a solid support with an oxazaphospholidine monomer of formula (3a) or (3b):

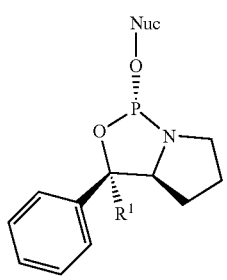

Formula 3a

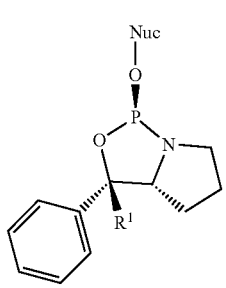

Formula 3b wherein $R^1$ is selected from hydrogen or $C_{1-4}$ alkyl.

In an embodiment, a pyridinium hydrobromide activator is used at about 0.25 M in acetonitrile for coupling of a nucleoside immobilized on a solid support with an oxazaphospholidine monomer of formula (3a) or (3b):

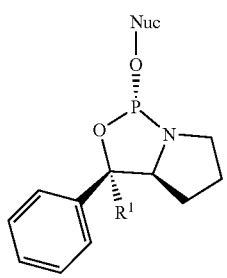

Formula 3a

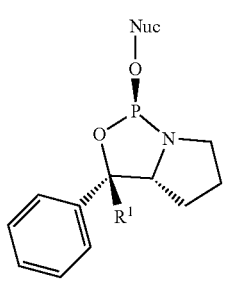

Formula 3b wherein $R^1$ is selected from hydrogen or $C_{1-4}$ alkyl.

Another aspect of the invention is an oligonucleotide manufactured according to the method of the invention.

In some embodiments B or B' is a nucleobase selected from the group consisting of adenine, guanine, cytosine, thymidine, uracil, xanthine, hypoxanthine, 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

In some embodiments, B or B' is a purine nucleobase. In some embodiments B or B' is a pyrimidine nucleobase. In some embodiments B or B' is adenine. In some embodiments, B or B' is thymidine. In some embodiments, B or B' is guanine. In some embodiments, B or B' is cytosine. In some embodiments, when B or B' is cytosine, B is 5-methylcytosine.

In some embodiments, B or B' is other than cytosine, for example, when the monomer is a D-DNA monomer, e.g. of formula 20 or 22. In some embodiments, e.g. when the monomer is a D-DNA-C, B is other than acetyl (Ac) protected cytosine.

It should be understood that for use in oligonucleotide synthesis the nucleobase group B or B' may be protected in the amidite monomers (thymidine is often used without a protection group). Suitable protection groups include dimethyformamide (DMF), dimethoxytrityl (DMT) or an acyl protection group, such as isobutyryl (iBu), or an acetyl protection group (Ac) or a benzoyl protection group (Bz).

In some embodiments, e.g. when the monomer is an L-LNA-G, B is other than DMF protected guanine (G). $R^3$=is selected from the group consisting of $CH_2ODMTr$, $CH_2$-Alkyl-O-DMTr, CH-Me-O-DMTr, $CH_2OMMTr$, $CH_2$-Alkyl-O-MMTr, CH(Me)-O-MMTr, CH—$R^a$—O-DMTr$R^b$, and CH—$R^a$—O-MMTr$R^b$;

$R^2$ is selected from the groups consisting of halo, such as —F, amino, azido, —SH, —CN, —OCN, —$CF_3$, —$OCF_3$, —O($R^m$)-alkyl, —S($R^m$)-alkyl, —N($R^m$)-alkyl, —O($R^m$)-alkenyl, —S($R^m$)-alkenyl, —N($R^m$)-alkenyl: —O($R^m$)-alkynyl, —S($R^m$)-alkynyl or —N($R^m$)-alkynyl; O-alkylenyl-O-alkyl, alkynyl, alkaryl, aralkyl, O-alkaryl, O-aralkyl, O$(CH_2)_2SCH_2$, O—$(CH_2)_2$—O—N($R^m$)($R^n$) or O—$CH_2C$(=O)—N($R^m$)($R^n$), —O—$(CH_2)_2OCH_3$, and —O—$CH_3$, where each $R^m$ and $R^n$ are independently, H, an amino protecting group or substituted or unsubstituted $C_{1-10}$ alkyl;

$R^4$ is selected from the group consisting of alkyl, cycloalkyl, cycloheteroalkyl, O-alkyl, S-alkyl, NH-alkyl, and hydrogen; In some embodiments, $R^4$ is hydrogen. In some embodiments, $R^4$ is hydrogen, and $R^2$ is selected from the group consisting of —O—$CH_3$, and —O—$(CH_2OCH_3$.

Or in some embodiments, $R^2$ and $R^4$ together designate a bivalent bridge, such as consisting of 1, 2, 3 groups/atoms selected from the group consisting of —C($R^aR^b$)—, —C($R^a$)=C($R^b$), —C($R^a$)=N, O, —Si($R^a$)$_2$—, S—, —$SO_2$—, —N($R^a$)—, and >C=Z;

wherein $R^a$ and, when present $R^b$, each is independently selected from hydrogen, optionally substituted $C_{1-6}$-alkyl, optionally substituted $C_{2-6}$-alkenyl, optionally substituted $C_{2-6}$-alkynyl, hydroxy, optionally substituted $C_{1-6}$-alkoxy, $C_{2-6}$-alkoxyalkyl, $C_{2-6}$-alkenyloxy, carboxy, $C_{1-6}$-alkoxycarbonyl, $C_{1-6}$-alkylcarbonyl, formyl, aryl, aryloxy-carbonyl, aryloxy, arylcarbonyl, heteroaryl, hetero-aryloxy-carbonyl, heteroaryloxy, heteroarylcarbonyl, amino, mono- and di($C_{1-6}$-alkyl)amino, carbamoyl, mono- and di($C_{1-6}$-alkyl)-aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, where aryl and heteroaryl may be optionally substituted and where two geminal substituents $R^a$ and $R^b$ together may designate optionally substituted methylene (=$CH_2$), wherein for all chiral centers, asymmetric groups may be found in either R or S orientation.

In some embodiments, when incorporated into an oligonucleotide, the nucleoside (Z) confers a higher binding affinity to a complementary RNA target than an equivalent DNA nucleoside. Such nucleosides are referred to as high affinity nucleosides. Examples of high affinity nucleosides include 2'-O-MOE, 2'-fluoro, 2'-O-methyl, and LNA nucleosides. In the embodiments, where the nucleoside is a high affinity nucleoside $R^3$ may, for example, be $CH_2$—O-DMTr or $CH_2$—O-MMTr.

In some embodiments. $R^2$ is selected from the group consisting of fluoro (—F). —O—$(CH_2)_2OCH_3$, and —O—$C_{1-3}$ alkyl, such as —O—$CH_3$. In such embodiments, optionally $R^4$ is hydrogen.

In some embodiments, the nucleoside is a LNA nucleoside (also known as a bicyclic nucleoside) comprising a 2'-4' bridge (biradicle).

In some embodiments, $R^2$ and $R^4$ together designate a bivalent bridge selected from the group consisting of bridge —C($R^aR^b$)—O—. —C($R^aR^b$) C($R^aR^b$)—O—, —$CH_2$—O—, —$CH_2CH_2$—O—, —CH($CH_3$)—O—. In some embodiments, $R^2$ and $R^4$ designate the bivalent bridge —$CH_2$—O-(methylene-oxy also known as oxy-LNA) or —CH($CH_3$)—O— (methyl-methylene-oxy). The —CH($CH_3$)—O— bridge introduces a chiral center at the carbon atom within the bridge, in some embodiments this is in the S position (for example a nucleoside known in the art as (S)cET—see EP1984381)). In some embodiments, $R^2$ and $R^4$ designate the bivalent bridge —$CH_2$—O— wherein the bridge is in the beta-D position (beta-D-oxy LNA). In some embodiments, $R^2$ and $R^4$ designate the bivalent bridge —$CH_2$—O— wherein the bridge is in the alpha-L position (alpha-L-D-oxy LNA). In some embodiments, $R^2$ and $R^4$ designate the bivalent bridge —$CH_2$—S— (thio LNA), or —$CH_2$—$NH_2$— (amino LNA). In the embodiments where $R^2$ and $R^4$ together designate a bivalent bridge, $R^3$ may, for example be $CH_2$—O-DMTr or $CH_2$—O-MMTr.

In some embodiments where the nucleoside (Nuc) is a bicyclic nucleotide (LNA) such as beta-D-oxy LNA, R is aryl, such as phenyl, and $R^1$ is hydrogen or $C_{1-3}$ alkyl. In such am embodiment, $R^5$ and $R^6$ may together form a heterocyclic ring, such as a five membered heterocyclic ring, as described herein (e.g. see formula 2a and 2b).

In some embodiments, the compound of formula (1a) or (1b) is selected from the group consisting of formula 4a, 4b, 5a, 5b, 6a, 6b, 7a and 7b.

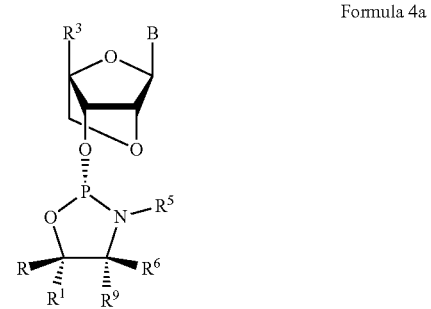

Formula 4a

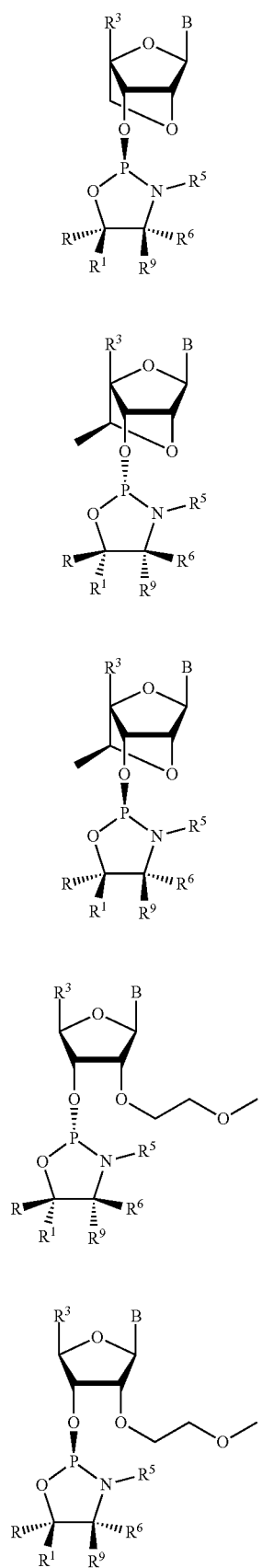
Formula 4b
Formula 5a
Formula 5b
Formula 6a
Formula 6b
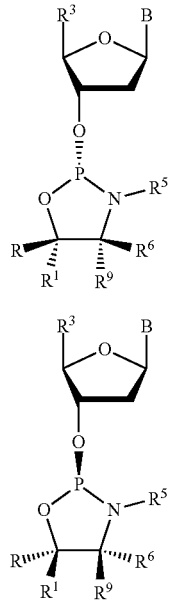
Formula 7a
Formula 7b
In some embodiments, the compound of formula (1a or 1b) is selected from the group consisting of formula 8a, 8b, 8c or 8d; or 9a, 9b, 9c or 9d:
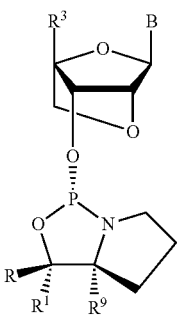
formula 8a
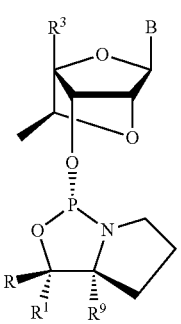
formula 8b
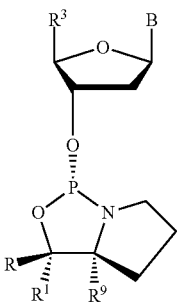
formula 8c

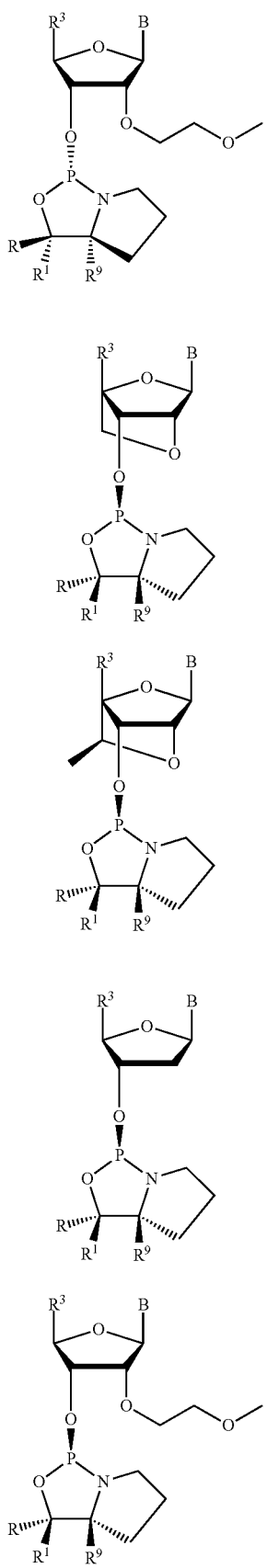

formula 8d formula 9a formula 9b formula 9c formula 9d

In some embodiments, the compound of formula (1a or 1b) is selected from the group consisting of formula of formula (10a) or (10b):

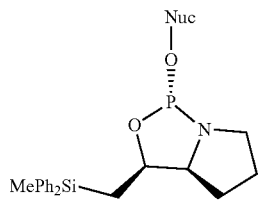

Formula 10a

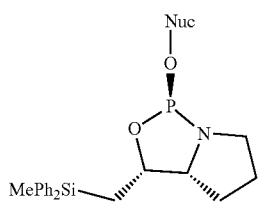

Formula 10b

In some embodiments, the nucleobase B is adenine, such as Bz protected adenine. In some embodiments, the nucleobase B is thymine. In some embodiments, the monomer is a D-DNA-A monomer (e.g. the monomer is of formula 9c and the nucleobase B is adenine, such as Bz protected adenine). The examples illustrate that D-DNA-A monomers (e.g. of formula 9c), L-LNA-A monomers and L-LNA-T monomers (e.g. of formula 8a or 8b) show improved coupling when used in acetonitrile/aromatic heterocyclic solvents, as according to the invention.

DMF Protected L-LNA-G

As illustrated in PCT/EP2017/060985, DMF protected L-LNA-G monomers are poorly soluble in acetonitrile solvents. An L-LNA monomer can be defined either by the stereochemistry of chiral auxiliary of the monomer, or the stereochemistry of the internucleoside linkage which the monomer forms when it is incorporated into an oligonucleotide (the two features are structurally linked, and L monomer results in the creation of a Sp phosphorothioate linkage). An L-LNA monomer is represented by formula 3a, wherein in $R^4$ and $R^2$ form $R^2$ and $R^4$ together designate a bivalent bridge. See for example the monomers of formula 4a, 5a, 8a and 8b.

In some embodiments, the oxazaphospholidine monomer is not an L-LNA monomer comprising a DMF protected guanine nucleobase.

In some embodiments the DMF protected guanine group (B) has the following structure:

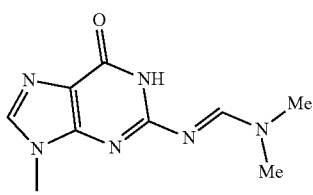 [SMILES: CN(C)/C=N/c1nc2c(ncn2C)c(=O)[nH]1]

In some embodiments, the oxazapholidine monomer is not a monomer of formula 11 or 12:

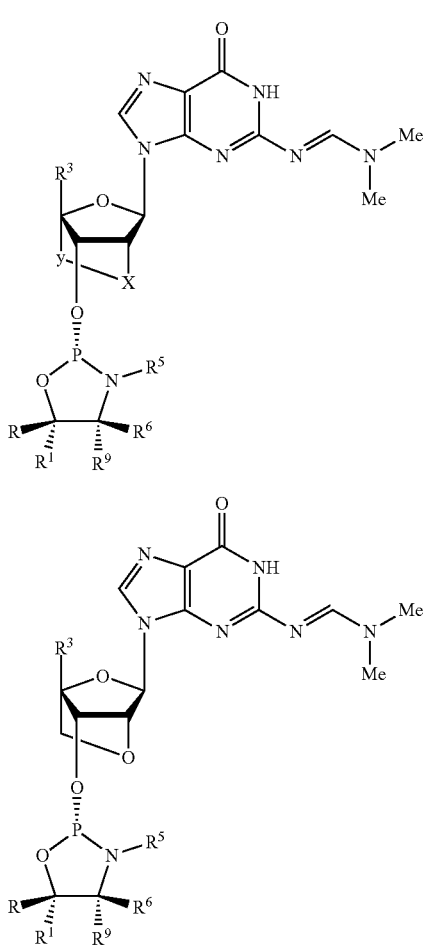

Formula 11

Formula 12

In some embodiments, the oxazapholidine monomer is a monomer of formula 13 or 14:

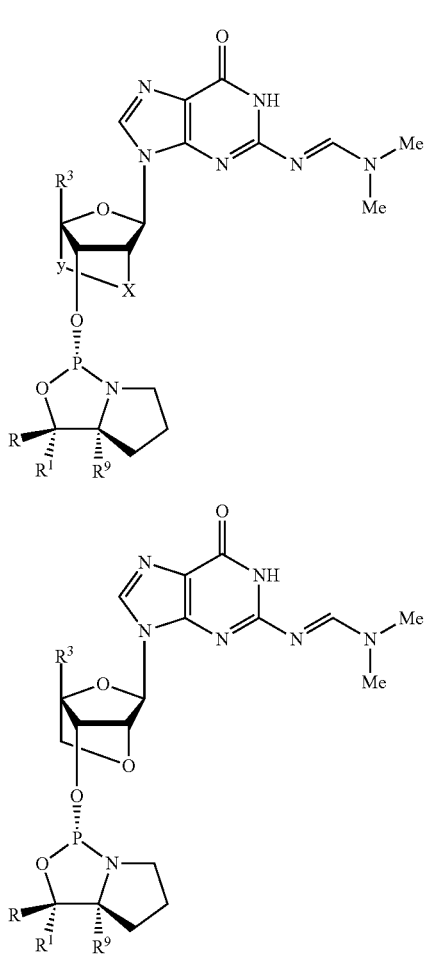

Formula 13

Formula 14 wherein R, $R^1$, $R^3$, $R^5$, $R^6$ & $R^9$ are as according to the monomer of formula 1, and wherein for the monomer of formula 11, X and Y together designate a bivalent bridge (e.g. as per $R^2$ and $R^4$ herein, such as a bridge selected from the group consisting of bridge —C($R^aR^b$)—O—, —C($R^aR^b$)C($R^aR^b$)—O—, —CH$_2$—O—, —CH$_2$CH$_2$—O—, —CH(CH$_3$)—O—. In some embodiments, X and Y designate the bivalent bridge —CH$_2$—O— (methylene-oxy also known as oxy-LNA) or —CH(CH$_3$)—O— (methyl-methylene-oxy). The —CH(CH$_3$)—O— bridge introduces a chiral center at the carbon atom within the bridge, in some embodiments this is in the S position (for example a nucleoside known in the art as (S)cET—see EP1984381)). In some embodiments, X and Y designate the bivalent bridge —CH$_2$—O— wherein the bridge is in the beta-D position (beta-D-oxy LNA). In some embodiments, X and Y designate the bivalent bridge —CH$_2$—O— wherein the bridge is in the alpha-L position (alpha-L-D-oxy LNA). In some embodiments, X and Y designate the bivalent bridge —CH$_2$—S— (thio LNA), or —CH$_2$—NH$_2$— (amino LNA). In the embodiments where X and Y together designate a bivalent bridge, $R^3$ may, for example be CH$_2$—O-DMTr or CH$_2$—O-MMTr.

Wherein X, Y, R, $R^1$, $R^9$ and $R^3$ are as per formula 11 and 12. The exocyclic oxygen of the guanine base may optionally be protected, e.g. with a cyano group.

In some embodiments, the oxazapholidine monomer is a monomer of formula or 16:

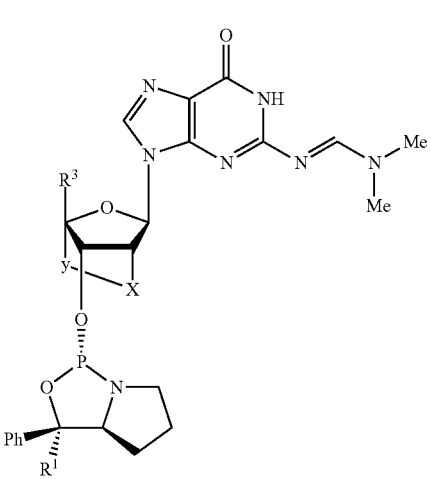

Formula 15

Formula 16

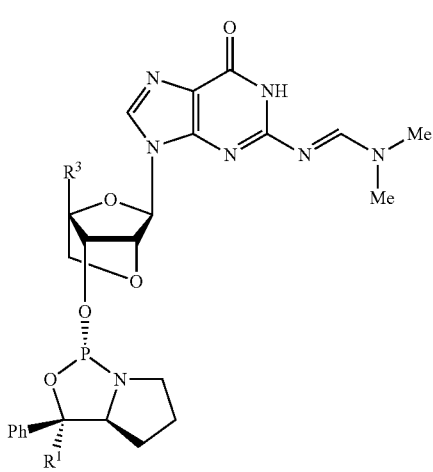

formula 24

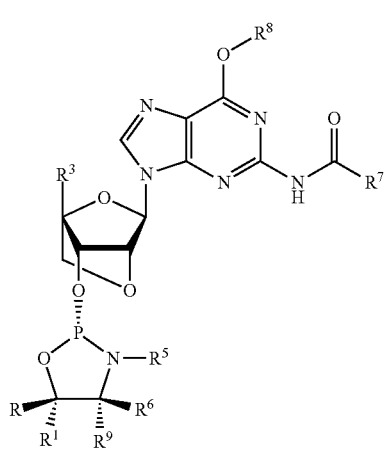

Wherein X, Y, R¹ and R³ are as per formula 11 and 12. The exocyclic oxygen of the guanine base may optionally be protected, e.g. with a cyano group. In some embodiments of formula 15 or 16, R¹ is hydrogen. In some embodiments of formula 15 or 16, R³ is $CH_2$—O-DMTr or $CH_2$—O-MMTr. In some embodiments, the oxazaphospholidine monomer of the invention comprises an acyl-protected nucleoside (Z).

Acyl Protected L-LNA-G

As illustrated in the examples, DMF protected L-LNA-G monomers are poorly soluble in acetonitrile solvents. However, we have previously identified that the use of acyl protection groups on the guanine nucleoside of L-LNA-G monomers overcomes the solubility problem.

In some embodiments, the oxazaphospholidine monomer is an L-LNA monomer comprising an acyl protected guanine nucleobase, such as an isobutyryl-protected guanine.

In some embodiments, the oxazaphospholidine monomer is an L-LNA-G monomer of formula 23, 24, 25, 26, 27, 28, 29 or 30:

formula 25

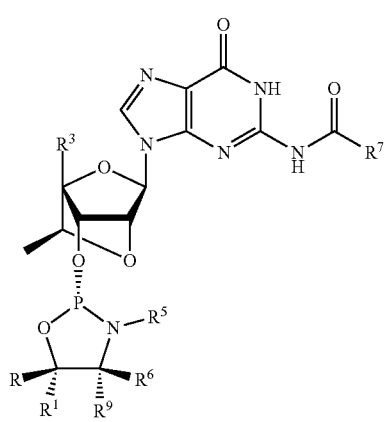

Formula 23

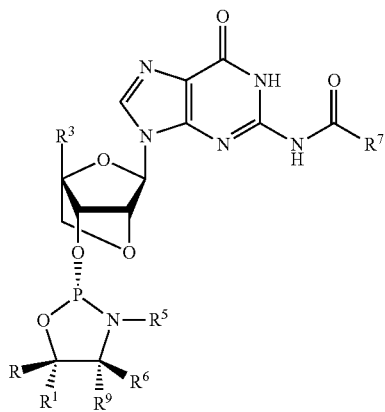

formula 26

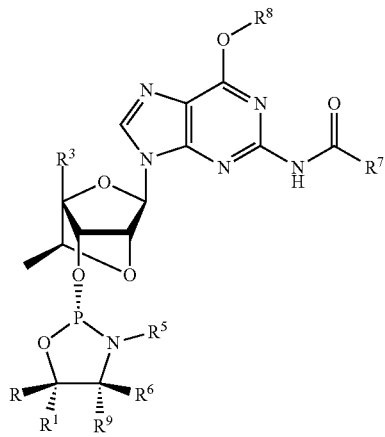

Formula 27

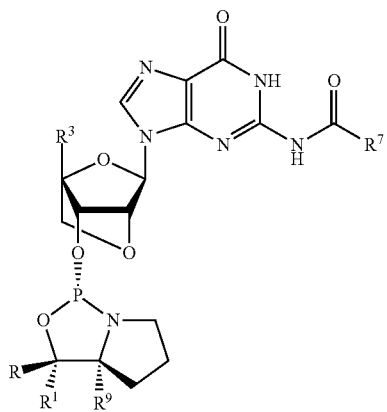

formula 28

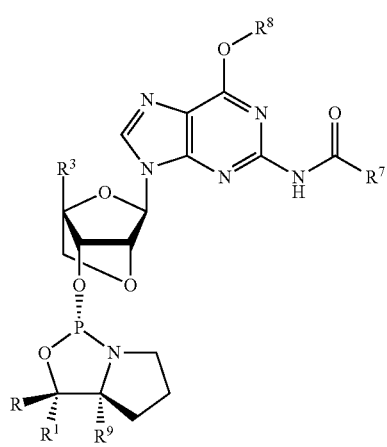

formula 29

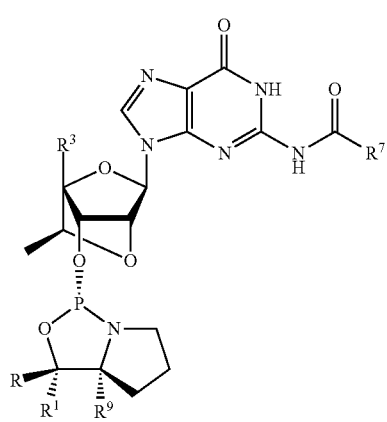

formula 30

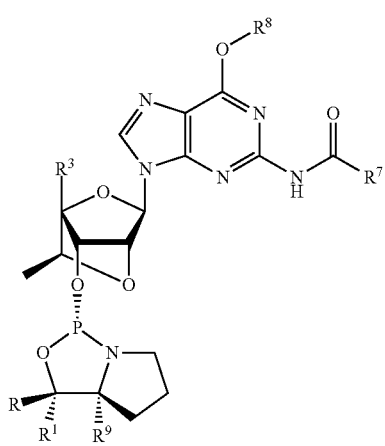

formula 31

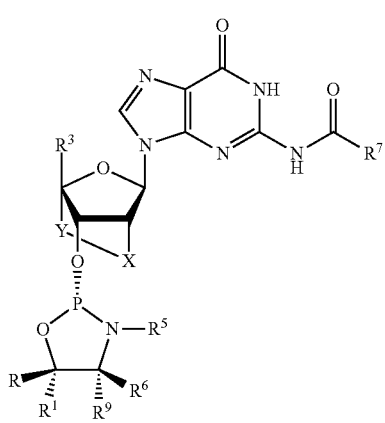

formula 32

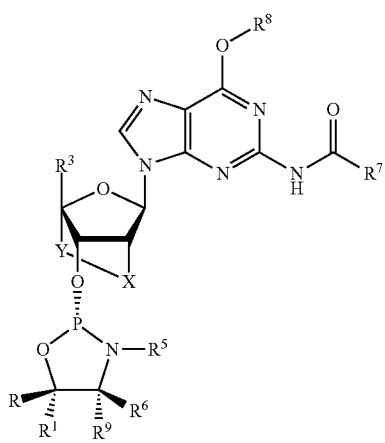

wherein, R, $R^1$, $R^2$, $R^3$, $R^4$, $R^5$, $R^9$ and $R^6$ are as per the compound of the invention, and —C(=O)—$R^7$ is the acyl protecting group on the exocyclic nitrogen of the guanine base, and $R^8$ when present is a protecting group on the guanine exocyclic oxygen. In some embodiments $R^8$ is cyanoethyl. In some embodiments, R is phenyl, $R^1$ is hydrogen or methyl, and $R^3$ is optionally $CH_2$—O-DMTr or $CH_2$—O-MMTr. In some embodiments, $R^7$ is isobutyryl. In formula's 31 and 32, Y and X are as per formula 11.

In some embodiments, the oxazaphospholidine monomer is selected from the group consisting of an L-LNA-T, D-DNA-A, D-DNA-C, L-LNA-C, and L-LNA-G (other than DMF protected L-LNA-G) or a L-DNA-C and L-DNA-T oxazaphospholidine monomer. As illustrated in the examples, these monomers show an improved coupling efficacy when used in the coupling solvent compositions of the invention, in addition to the solubility and stability benefits seen with in general for oxazapholidine monomers.

Solvent Compositions (solutions)

In some embodiments, the coupling step b) of the method of the invention uses an acetonitrile solution comprising an oxazapholidine monomer, acetonitrile and an aromatic heterocyclic solvent.

In some embodiments, the acetonitrile solution further comprises an activator. Numerous activators for use in phosphoramidite oligonucleotide synthesis are known—they typically comprise acidic azole catalysts, such as 1H-tetrazole, 5-ethylthio-1H-tetrazole, 2-benzylthiotetrazole, and 4,5-dicyanoimidazole. These activators are not necessarily useful in oxazapholidine synthesis.

In some embodiments, the aromatic heterocyclic solvent has a pKa of about 4-about 7. In some embodiments, the aromatic heterocyclic solvent has a pKa of about 7-about 17 in water at 20° C.

In some embodiments, the aromatic heterocyclic solvent is an aromatic heterocyclic base.

In some embodiments, the aromatic heterocyclic solvent is an aromatic heterocyclic acid.

In some embodiments, the aromatic heterocyclic solvent is selected from the group consisting of pyridine, 2-picoline, 4-picoline, 3-picoline, lutidine, and pyrrole.

In some embodiments, the aromatic heterocyclic solvent is pyridine.

In some embodiments, the aromatic heterocyclic solvent is pyrrole.

In some embodiments, the aromatic heterocyclic solvent is 3-picoline.

In some embodiments, the concentration (v/v), of aromatic heterocyclic solvent in acetonitrile is between about 0.1% and about 50% (v/v). In some embodiments, the concentration (v/v), of aromatic heterocyclic solvent in acetonitrile is between about 0.5% and about 40% (v/v). In some embodiments, the concentration (v/v), of aromatic heterocyclic solvent in acetonitrile is between about 0.5% and about 30% (v/v). In some embodiments, the concentration (v/v), of aromatic heterocyclic solvent in acetonitrile is between about 0.5% and about 25% (v/v). In some embodiments, the concentration (v/v), of aromatic heterocyclic solvent in acetonitrile is between about 0.5% and about 10% (v/v). In some embodiments, the concentration (v/v), of aromatic heterocyclic solvent in acetonitrile is between about 0.5% and about 5% (v/v). In some embodiments, the concentration (v/v), of aromatic heterocyclic solvent in acetonitrile is between about 1% and about 5% (v/v). In some embodiments, the concentration (v/v), of aromatic heterocyclic solvent in acetonitrile is between about 1% and about 4% (v/v). In some embodiments, the concentration (v/v), of aromatic heterocyclic solvent in acetonitrile is between about 0.5% (v/v) and about 10% (v/v), such as between about 1% (v/v) and about 5% (v/v), such as between about 2-3% (v/v), such as about 2.5% (v/v). In these embodiments, optionally the aromatic heterocyclic base solvent is pyridine.

In some embodiments, wherein the aromatic heterocyclic solvent is pyridine, the concentration (v/v), of aromatic heterocyclic solvent in acetonitrile is between about 0.5% and about 10%, such as between about 1% and about 5%, such as between about 2-3%, such as about 2.5% or about 3.5%, or between about 2-4%.

In some embodiments, wherein the aromatic heterocyclic solvent is pyrrole, the concentration (v/v), of aromatic heterocyclic solvent in acetonitrile is between about 0.5% and about 10%, such as between about 1% and about 5%, such as between 2-4% or about 2-3%, such as about 2.5%.

In some embodiments, wherein the aromatic heterocyclic solvent is 3-picoline, the concentration (v/v), of aromatic heterocyclic solvent in acetonitrile is between about 0.5% and about 10%, such as between about 1% and about 5%, such as between 2-4%, or about 2-3%, such as about 2.5%.

Pyridinium Acidic Salt Activators

Activators are reagents used prior to or during the coupling step of oligonucleotide synthesis which activate the oxazapholidine monomer to allow coupling of the monomer to the 5' terminal group attached to the solid support or oligonucleotide chain.

In the method of the invention the activator is a pyridinium acidic salt. Pyridinium acidic salts can be selected from the group consisting of as pyridinium hydroiodide, pyridinium camphor sulphonic acid, pyridinium hydrochloride, pyridinium hydrobromide, pyridinium trifluroacetate, pyridinium triflate and pyridinium mesylate. Other pyridinium acidic salts can also be used Additional Activators Other activators can be added in addition, for example, in some embodiments, the additional activator is selected from the group consisting of CMPT (N-(Cyanomethyl)pyrrolidinium triflate (CMPT). N-(phenyl)imidazolium triflate (PhIMT), benzimidazolium triflate (BIT), 4,5-dicyanoimidazole (DCI), tetrazole, and 5-(Benzylthio)-1H-tetrazole.

In some embodiments, the additional activator is 4,5-dicyanoimidazole (DCI).

In some embodiments, the solvent composition comprises about 0.5-about 2M DCI (or the other activators of claim 13), such as about 1 M DCI (or the other activators of claim 13).

In some embodiments, the solvent composition further comprises N-methylimidazole, such as N-methylimidazole in a concentration of 0.01-about 1 M N-methylimidazole, such as about 0.1M N-methylimidazole.

In some embodiments, the activator comprises N-methylimidazole. In some embodiments, the activator comprises 4,5-dicyanoimidazole (DCI), tetrazole, or 5-(Benzylthio)-1H-tetrazole. In some embodiments, the activator comprises 4,5-dicyanoimidazole (DCI), tetrazole, or 5-(Benzylthio)-1H-tetrazole and N-methylimidazole.

In some embodiments, the concentration of N-methylimidazole used is 0.01M-about 1M N-methylimidazole, such as about 0.1M N-methylimidazole. In some embodiments, the acetonitrile solution comprises N-methylimidazole in a concentration of 0.01M-about 1M N-methylimidazole, such as about 0.1M N-methylimidazole.

In some embodiments, the activator is DCI or tetrazole, or 5-(Benzylthio)-1H-tetrazole, which may be used at a concentration (e.g. in the acetonitrile solution of the invention) of about 0.5-about 2M, such as about 1M.

The stereodefined, sugar modified oligonucleotides that are synthesized according to the invention can be oligonucleotides that comprise 2'-sugar modified oligonucleosides. In other words, they can be 2'-sugar modified oligonucleotides.

The stereodefined, sugar modified oligonucleotides that are synthesized according to the invention can be oligonucleotides that comprise Locked Nucleic Acid Nucleosides (LNA nucleosides). In other words, they can be Locked Nucleic Acid Nucleotides (LNA nucleotides).

In some embodiments the activator is 4,5-dicyanoimidazole (DCI). In some embodiments, the solvent composition comprises about 0.5-about 2M DCI, such as about 1M DCI. It will be recognised that in order to optimise coupling efficacy, it may be necessary to optimize the amount of activator used, as is illustrated in the examples. In some embodiments the concentration of DCI activator uses is between 0.5M and 1M DCI. In some embodiments when the activator is DCI, the solvent composition further comprises N-methylimidazole (NMI), such as N-methylimidazole in a concentration of 0.01-about 1M N-methylimidazole, such as about 0.1M N-methylimidazole. NMI is an agent which can enhance the solubility of other activators such as DCI.

Figures 1A, 1B, 1C, 1D, 1E:
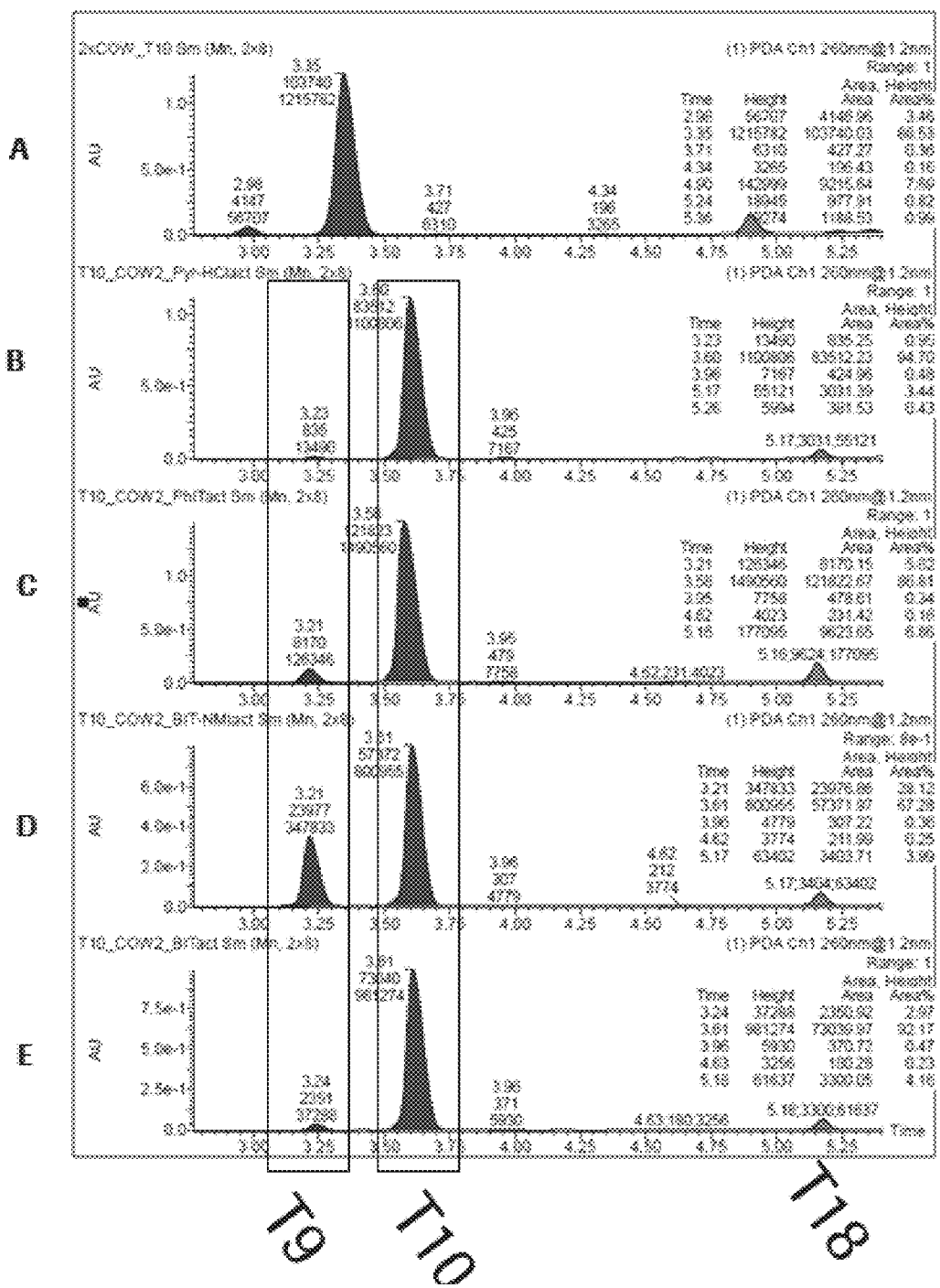
FIG. 1 depicts a series of graphs, FIGS. 1A, 1B, 1C, 1D and 1E, based on an Ultra Performance Liquid Chromatography—mass spectrometry tandem analysis. The graphs exhibit the analysis of the crude material after coupling of a 9-mer fully phosphorothioated DNA T oligonucleotide with a L-DNA T monomer using various coupling activators and solvents to obtain a 10-mer oligonucleotide in a method according to the invention.

The method of the invention provides a path to the synthesis of stereodefined oligonucleotides with a higher coupling efficiency than in the prior art as evidenced by the experiments conducted by the inventors. A non-limiting example of a generic process for preparing stereodefined oligonucleotides is depicted on FIG. 8. Referring to example 1 and FIG. 1 that summarize the experiments conducted by the inventors, it can be seen that the coupling of a 9-mer with a monomer to obtain a 10-mer gives a better yield with a pyridinium hydrochloride salts (94.7%) than with other non pyridinium acidic salt activators such as DCI+NMI, phenyl imidazolium triflate, benzimidazolium triflate+NMI or benzimidazolium triflate. Referring to FIG. 1B, the peaks of the resulting 10-mer and remaining 9-mer and by-product di-mer (18-mer) are more favourable than with the other coupling activators.

Figures 2A, 2B, 2C:
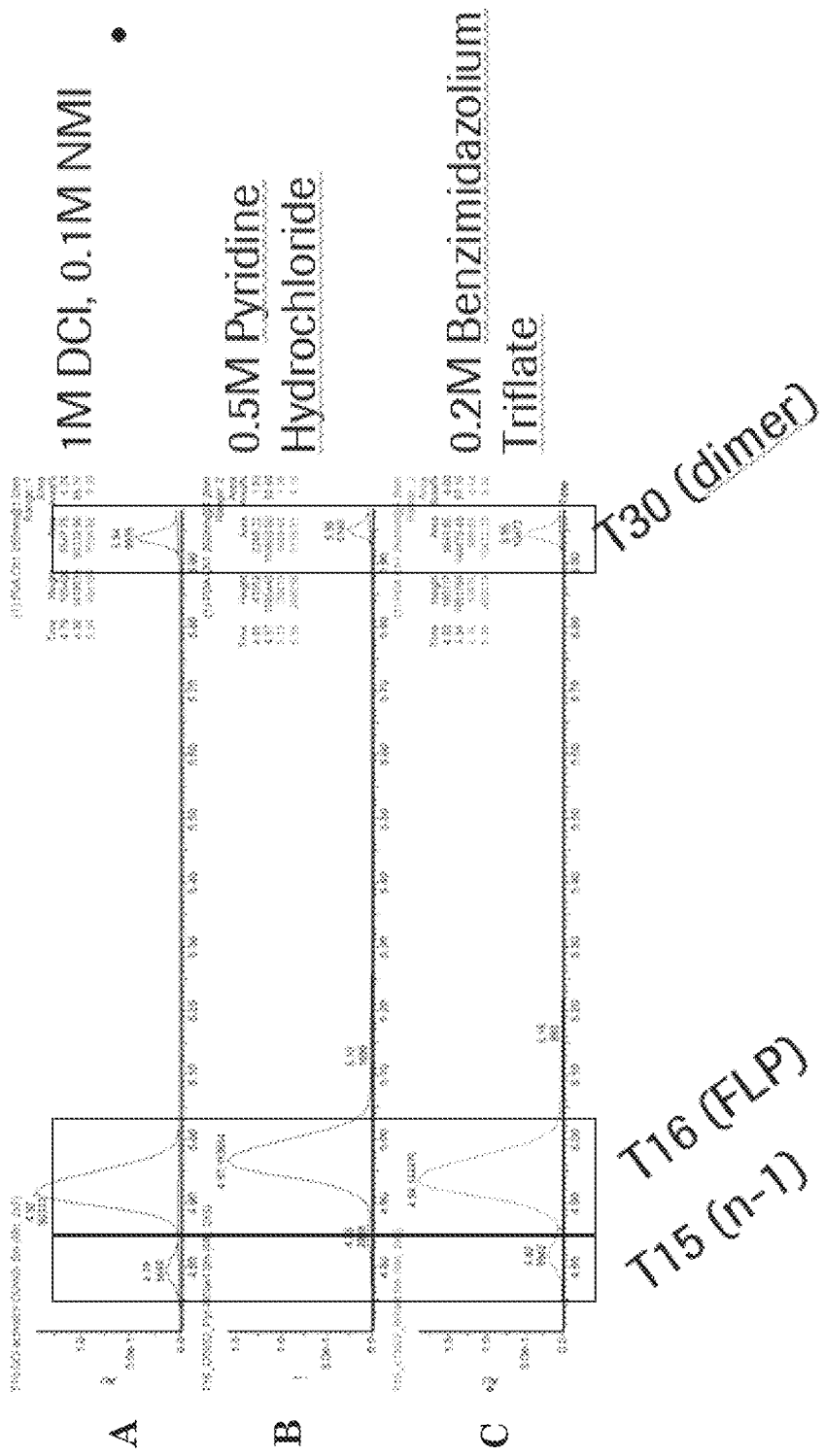

The same is shown with example 2 and FIG. 2, in particular FIG. 1B.

Examples 3, 4 and FIGS. 3, 4 also evidence the superiority of pyridinium acidic salt activators at various concentrations over DCI+NMI.

Examples 5, 6 and FIGS. 5, 6 show that pyridinium hydrobromide is particularly efficient among others pyridinium acidic salt activators.

FIG. 7 shows the theoretical overall reaction yields of oligomers as a function of different activators and lengths of oligonucleotides as per FIG. 6. This figure shows that small changes in coupling yields have dramatic effects on overall oligomer yield.

The following non-limiting examples will further illustrate the invention.

EXAMPLES

Example 1

To examine the effect of the activator on the coupling efficiency and overall coupling purity a single coupling reaction of L-DNA T was performed on a solid support onto which a 9-mer fully phosphorothioated DNA T previously had been synthesized with the use of stereorandom 2-cyanoethyl phosphoramidites. The synthesis took place on an AKTA OligoPilot 100 in 0.2 µmol scale. 2 coupling reactions (10 minutes coupling time) were performed with a thiolation and washing step in between the two coupling reactions, followed by thiolation, capping and detritylation. Hereafter, the solid support was treated with 20% Diethylamine in acetonitrile.

The activator was selected from one of the following as indicated in the figure.

A) 1 M 4,5-Dicyanoimidazole (DCI)+0.1 N-methylimidazole (NMI)
B) 0.5 M Pyridinium hydrochloride in MeCN
C) 0.2 M N-Phenyl imidazolium triflate in MeCN
D) 0.2 M benzimidazolium triflate in MeCN+0.1 M NMI
E) 0.2 M benzimidazolium triflate in MeCN L-DNA T was dissolved in a solution of 3.5% pyridine in MeCN at 0.15 M concentration. Sulfurization was carried out using 0.1 M Xanthane hydride in pyridine: MeCN (1:1), capping was carried out using 20% NMI in MeCN in Cap A and Pyridine/Ac2O/MeCN (3:5:2) as Cap B. Detritylation was carried out using 3% V/V dichloroacetic acid in dichloromethane The oligonucleotide was globally deprotected using concentrated aq. ammonium hydroxide at 55° C. for 24 h. The crude material was analyzed by UPLC-MS analysis. The chromatogram detected by UV absorbance at 260 nm primarily consisted of three peaks, the Full-length T10 oligomer, the T9 oligomer resulting from a failed coupling reaction and a T18 oligomer, resulting as impurity from the coupling reaction. These 3 peaks were quantified by integrating the absorbance of the peak at 260 nm, and are given below as a function of the activator used for the coupling reaction.

| Activator | % UV T9 oligomer | % UV T10 oligomer | % UV T18 oligomer |
| --- | --- | --- | --- |
| A | 3.5% | 86.5% | 7.7% |
| B | 1.0% | 94.7% | 3.4% |
| C | 5.8% | 86.8% | 6.9% |
| D | 28.1% | 67.3% | 4.0% |
| E | 3.0% | 92.2% | 4.2% |

It is seen that the highest % UV of the desired T10 oligomer is obtained for activator B (0.5 M Pyridinium hydrochloride in MeCN) with the lowest level of T9 coupling failure species, and T18 impurity.

Example 2

To examine the effect of the activator on the coupling efficiency and overall coupling purity a single coupling reaction of L-DNA T was performed on a solid support onto which a 15-mer fully phosphorothioated DNA T previously had been synthesized with the use of stereorandom 2-cyanoethyl phosphoramidites. The synthesis took place on a AKTA OligoPilot 100 in 0.2 µmol scale. 2 coupling reactions (10 minutes coupling time) were performed with a thiolation and washing step in between the two coupling reactions, followed by thiolation, capping and detritylation. Hereafter, the solid support was treated with 20% Diethylamine in acetonitrile.

The activator was selected from one of the following as indicated in the figure.

A) 1 M 4,5-Dicyanoimidazole (DCI)+0.1 N-methylimidazole (NMI)
B) 0.5 M Pyridinium hydrochloride in MeCN
C) 0.2 M N-Phenyl imidazolium triflate in MeCN
D) 0.2 M benzimidazolium triflate in MeCN+0.1 M NMI
E) 0.2 M benzimidazolium triflate in MeCN L-DNA T was dissolved in a solution of 3.5% pyridine in MeCN at 0.15 M concentration. Sulfurization was carried out using 0.1 M Xanthane hydride in pyridine: MeCN (1:1), capping was carried out using 20% NMI in MeCN in Cap A and Pyridine/Ac2O/MeCN (3:5:2) as Cap B. Detritylation was carried out using 3% V/V dichloroacetic acid in dichloromethane The oligonucleotide was globally deprotected using concentrated aq. ammonium hydroxide at 55° C. for 24 h. The crude material was analyzed by UPLC-MS analysis. The chromatogram detected by UV absorbance at 260 nm primarily consisted of three peaks, the Full-length T16 oligomer, the T15 oligomer resulting from a failed coupling reaction and a T30 oligomer, resulting as impurity from the coupling reaction. These 3 peaks were quantified by integrating the absorbance of the peak at 260 nm, and are given below as a function of the activator used for the coupling reaction.

| Activator | % UV T15 oligomer | % UV T16 oligomer | % UV T30 oligomer |
|---|---|---|---|
| A | 5.2% | 85.4% | 9.4% |
| B | 1.8% | 92.6% | 4.2% |
| E | 6.0% | 87.15 | 6.32 |

It is seen that the highest % UV of the desired T16 oligomer is obtained for activator B (0.5 M Pyridinium hydrochloride in MeCN) with the lowest level of T15 coupling failure species, and T30 impurity.

Example 3

To examine the effect of the activator on the coupling efficiency a single coupling reaction of L-LNA T was performed on a solid support onto which a 15-mer fully phosphorothioated DNA T previously had been synthesized with the use of stereorandom 2-cyanoethyl phosphoramidites. The synthesis took place on a AKTA OligoPilot 100 in 0.2 µmol scale. 2 coupling reactions (10 minutes coupling time) were performed with a thiolation and washing step in between the two coupling reactions, followed by thiolation, capping and detritylation. Hereafter, the solid support was treated with 20% Diethylamine in acetonitrile.

The activator was selected from one of the following as indicated in the figure.
- A) 1 M 4,5-Dicyanoimidazole (DCI)+0.1 N-methylimidazole (NMI)
- B) 0.5 M Pyridinium hydrochloride in MeCN
- C) 0.25 M Pyridinium hydrochloride in MeCN
- D) 0.25 M Pyridinium hydrobromide in MeCN
- L-LNA T was dissolved in a solution of 3.5% pyridine in MeCN at 0.15 M concentration. Sulfurization was carried out using 0.1 M Xanthane hydride in pyridine:MeCN (1:1), capping was carried out using 20% NMI in MeCN in Cap A and Pyridine/Ac2O/MeCN (3:5:2) as Cap B. Detritylation was carried out using 3% V/V dichloroacetic acid in dichloromethane The oligonucleotide was globally deprotected using concentrated aq. ammonium hydroxide at 55° C. for 24 h. The crude material was analyzed by UPLC-MS analysis. The UV absorbance of the full length product peak was compared to the UV absorbance of the T15 peak, to obtain a relative measure of coupling efficiency.

| Activator | Coupling efficiency |
|---|---|
| A | 71.2% |
| B | 91.9% |
| C | 77.3% |
| D | 96.9% |

It is seen that the highest coupling efficiency is achieved with activator D (0.25 M Pyridinium hydrobromide in MeCN), despite the concentration of the activator has been lowered to 0.25M compared to pyridinium hydrochloride.

Example 4

To examine the effect of the activator on the coupling efficiency a single coupling reaction of L-LNA $^m$C was performed on a solid support onto which a 15-mer fully phosphorothioated DNA T previously had been synthesized with the use of stereorandom 2-cyanoethyl phosphoramidites. The synthesis took place on a AKTA OligoPilot 100 in 0.2 µmol scale. 2 coupling reactions (10 minutes coupling time) were performed with a thiolation and washing step in between the two coupling reactions, followed by thiolation, capping and detritylation. Hereafter, the solid support was treated with 20% Diethylamine in acetonitrile.

The activator was selected from one of the following as indicated in the figure.
- A) 1 M 4,5-Dicyanoimidazole (DCI)+0.1 N-methylimidazole (NMI)
- B) 0.5 M Pyridinium hydrochloride in MeCN
- C) 0.25 M Pyridinium hydrobromide in MeCN
- L-LNA $^m$C was dissolved in a solution of 3.5% pyridine in MeCN at 0.15 M concentration. Sulfurization was carried out using 0.1 M Xanthane hydride in pyridine:MeCN (1:1), capping was carried out using 20% NMI in MeCN in Cap A and Pyridine/Ac2O/MeCN (3:5:2) as Cap B. Detritylation was carried out using 3% V/V dichloroacetic acid in dichloromethane The oligonucleotide was globally deprotected using concentrated aq. ammonium hydroxide at 55° C. for 24 h. The crude material was analyzed by UPLC-MS analysis. The UV absorbance of the full length product peak was compared to the UV absorbance of the T15 peak, to obtain a relative measure of coupling efficiency.

| Activator | Coupling efficiency |
|---|---|
| A | 53.3% |
| B | 76.8% |
| C | 83.6% |

It is seen that the highest coupling efficiency is achieved with activator C (0.25 M Pyridinium hydrobromide in MeCN).

Example 5

To examine the effect of the activator on the coupling efficiency a single coupling reaction of L-LNA $^m$C was performed on a solid support onto which a 15-mer fully phosphorothioated DNA T previously had been synthesized with the use of stereorandom 2-cyanoethyl phosphoramidites. The synthesis took place on a AKTA OligoPilot 100 in 0.2 µmol scale. 2 coupling reactions (20 minutes coupling time) were performed with a thiolation and washing step in between the two coupling reactions, followed by thiolation, capping and detritylation. Hereafter, the solid support was treated with 20% Diethylamine in acetonitrile.

The activator was selected from one of the following as indicated in the figure.
- A) 0.5 M Pyridinium hydrochloride in MeCN
- B) 0.25 M Pyridinium hydrobromide in MeCN
- L-LNA $^m$C was dissolved in a solution of 3.5% pyridine in MeCN at 0.15 M concentration. Sulfurization was carried out using 0.1 M Xanthane hydride in pyridine:MeCN (1:1), capping was carried out using 20% NMI in MeCN in Cap A and Pyridine/Ac2O/MeCN (3:5:2)

as Cap B. Detritylation was carried out using 3% V/V dichloroacetic acid in dichloromethane The oligonucleotide was globally deprotected using concentrated aq. ammonium hydroxide at 55° C. for 24 h. The crude material was analyzed by UPLC-MS analysis. The UV absorbance of the full length product peak was compared to the UV absorbance of the T15 peak, to obtain a relative measure of coupling efficiency.

| Activator | Coupling efficiency |
|---|---|
| A | 87.1% |
| B | 91.0% |

It is seen that the highest coupling efficiency is achieved with activator B (0.25 M Pyridinium hydrobromide in MeCN), and it is also seen that an increased coupling time leads to increased coupling efficiencies compared to example 4.

Example 6

To examine the effect of the activator on the coupling efficiency a single coupling reaction of L-LNA $^m$C was performed on a solid support onto which a 15-mer fully phosphorthioated DNA T previously had been synthesized with the use of stereorandom 2-cyanoethyl phosphoramidites. The synthesis took place on a AKTA OligoPilot 100 in 0.2 μmol scale. 2 coupling reactions (20 minutes coupling time) were performed with a thiolation and washing step in between the two coupling reactions, followed by thiolation, capping and detritylation. Hereafter, the solid support was treated with 20% Diethylamine in acetonitrile.

The activator was selected from one of the following as indicated in the figure.
A) 0.5 M Pyridinium hydrochloride in MeCN
B) 0.25 M Pyridinium hydrobromide in MeCN
C) 0.25M Pyridinium trifluoroacetate
D) 0.25M Pyridinium para-toluenesulfonate
E) 0.25 M Pyridinium triflate
L-LNA $^m$C was dissolved in a solution of 3.5% pyridine in MeCN at 0.15 M concentration. Sulfurization was carried out using 0.1 M Xanthane hydride in pyridine:MeCN (1:1), capping was carried out using 20% NMI in MeCN in Cap A and Pyridine/Ac2O/MeCN (3:5:2) as Cap B. Detritylation was carried out using 3% V/V dichloroacetic acid in dichloromethane The oligonucleotide was globally deprotected using concentrated aq. ammonium hydroxide at 55° C. for 24 h. The crude material was analyzed by UPLC-MS analysis. The UV absorbance of the full length product peak was compared to the UV absorbance of the T15 peak, to obtain a relative measure of coupling efficiency.

| Activator | Coupling efficiency |
|---|---|
| A | 87.1% |
| B | 91.0% |
| C | 68.7% |
| D | 81.8% |
| E | 80.3% |

Example 7

A 50 μmol scale synthesis was carried out using 393 μmol/g Kinnovate resine on an Äkta OligoPilot 10. Using conventional 5'-dimethoxytrityl-3'-β-cyanoethyl phosphoramidites, 12 stereorandom couplings 5'-CGATCGATCGAT-3' were carried out, followed by four stereodefined couplings (C*A*G*T*) depicted bellow. All stereodefined monomers were dissolved in 3.5% pyridine in acetonitrile

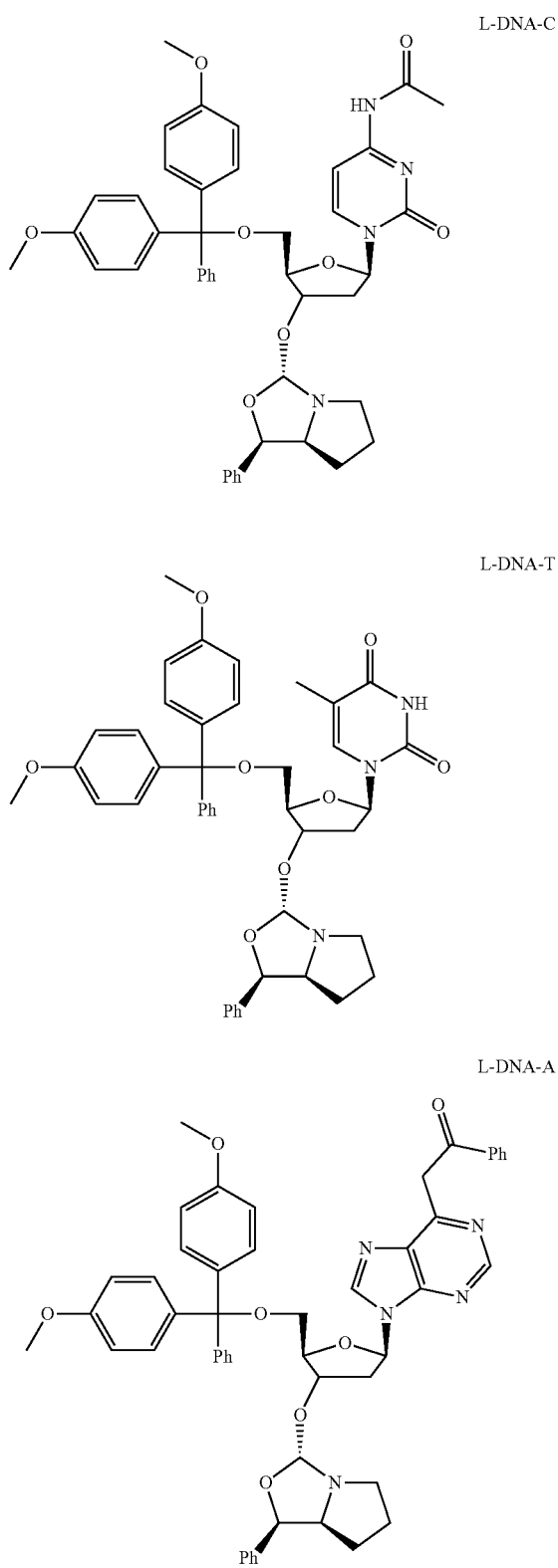

-continued

L-DNA-G

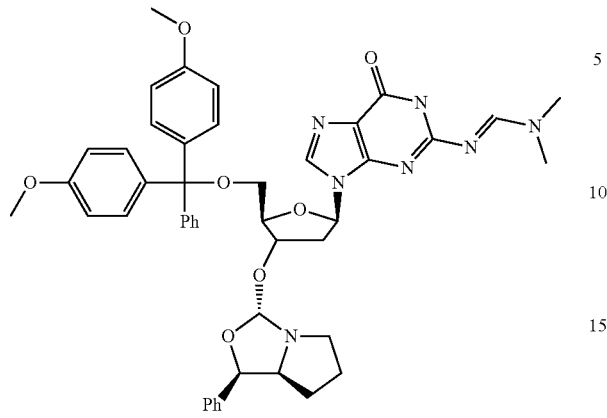

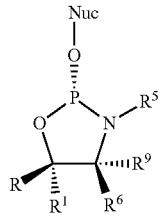

Formula 1a

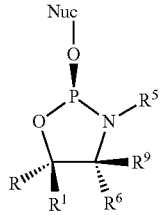

Formula 1b

All synthetic steps were carried out according to a standard oligonucleotides synthesis:
Detritylation
Coupling
Oxydation/Sulphurization
Capping
Reagents used in the synthetic cycle:
Deblock: 3% Dichloroacetic acid in toluene (v/v)
Activator: see table below
Stereorandom phosphoramidites: 0.2 M solution in Acetonitrile
Stereodefined phosphoramidites: see table below
Cap A: N-Methylimidazole/Acetonitrile 2/8 (v/v)
Cap B1: Acetic Anhydride/Acetonitrile 4/6 (v/v)
Cap B2: Pyridine/Acetonitrile 6/4 (v/v)
Sulfurizing reagent: 0.1M Xanthane hydride in Acetonitrile/Pyridine 1/1 (v/v)
Oxidizer: Iodine/Water/Pyridine 12.7/1/9 (w/v/v)

After completion of the oligonucleotides synthesis, a deprotection/cleavage step is carried out in a solution of 32% Ammonia in water at 65° C. for 6 h. The results of the optimization are depicted in the table below:

In the table below the sequence of coupling, oxidation, wash (COW) was used in cases where more than one coupling was performed.

| Activators | | Equivalents (a/c/g/t resp.) | | | | Recy. (m) | Yield (%) |
|---|---|---|---|---|---|---|---|
| PyrBr | 0.25M | 2 × 2eq. | 2 × 2eq. | 2 × 2eq. | 2 × 2eq. | 10 | 15 |
| PyrOtf | 0.25M | 2 × 2eq. | 2 × 2eq. | 2 × 2eq. | 2 × 2eq. | 10 | 8 |
| PyrOTf | 1M | 1 × 5eq. | 1 × 5eq. | 1 × 5eq. | 1 × 5eq. | 10 | 23 |
| PyrBr | 0.5M | 1 × 5eq. | 1 × 5eq. | 1 × 5eq. | 1 × 5eq. | 10 | 11 |
| CMPT | 1M | 1 × 5eq. | 1 × 5eq. | 1 × 5eq. | 1 × 5eq. | 10 | 18 |
| PyrOTf | 0.5M | 1 × 5eq. | 1 × 5eq. | 1 × 5eq. | 1 × 5eq. | 10 | 17 |
| PyrOTf | 0.3M | 1 × 5eq. | 1 × 5eq. | 1 × 5eq. | 1 × 5eq. | 10 | 23 |
| PyrBr | 0.3M | 1 × 5eq. | 1 × 5eq. | 1 × 5eq. | 1 × 5eq. | 10 | 22 |
| PyrOTf | 0.3M | 1 × 5eq. | 1 × 5eq. | 1 × 5eq. | 1 × 5eq. | 20 | 24 |

CMPT: N-(Cyanomethyl)-pyrrolidinium triflate
Pyr: Pyridinium
OTf: Trifluoromethane sulfonate

The invention claimed is:

1. A method for the synthesis of stereodefined, sugar modified oligonucleotides comprising a step of coupling an oxazaphospholidine monomer of formula (1a) or (1b):

wherein Nuc is a nucleoside comprising a protected 5'-hydroxyl and is attached to the oxygen atom of Formula 1a or 1b via its 3' position;
R is selected from the groups consisting of nitro, halogen, cyano, silyl, sulfone, $C_{1-4}$ alkyl, $C_{1-4}$ alkylsulfone, $C_{6-14}$ arylsulfone, $C_{6-14}$ aryl, $C_{5-14}$ heteroaryl comprising one, two or three heteroatoms independently selected from O, N or S, each of the silyl, alkyl, aryl, heteroaryl moieties can be unsubstituted or substituted by one or more group(s) selected from the group consisting of: $C_{1-4}$ alkyl, $C_{6-14}$ aryl and $C_{1-4}$, alkoxy or silyl substituted by one or more substituent selected from $C_{1-4}$-alkyl and $C_{6-14}$ aryl;
$R^1$ is selected from hydrogen or $C_{1-4}$ alkyl; and
$R^5$, $R^6$ and $R^9$ are independently selected from the group consisting of hydrogen, $C_{1-4}$ alkyl, $C_{5-6}$ cycloalkyl, $C_{6-14}$ aryl, $C_{5-14}$ heteroaryl comprising one, two or three heteroatoms independently selected from O, N or S, each of which alkyl, cycloalkyl, aryl or heteroaryl can be substituted by one, two or three substituents selected from the group consisting of $C_{1-4}$ alkyl, $C_{6-14}$ aryl and $C_{1-4}$, alkoxy:
or two of $R^5$, $R^6$ or $R^9$ together form a heterocyclic ring comprising 3-7 carbon atoms, together with the N atom to which $R^5$ is attached, wherein said heterocyclic ring can be substituted by one, two or three substituents selected from the group consisting of $C_{1-4}$ alkyl, $C_{6-14}$ aryl and $C_{1-4}$, alkoxy,
with a nucleoside immobilized on a solid support wherein the coupling is performed in the presence of a pyridinium acidic salt coupling activator, wherein the pyridinium acidic salt coupling activator is pyridinium hydrochloride or pyridinium hydrobromide.

2. The method of claim 1, wherein the pyridinium acidic salt coupling activator is pyridinium hydrochloride.

3. The method of claim 1, wherein the pyridinium acidic salt coupling activator is pyridinium hydrobromide.

4. The method of claim 1, wherein the pyridinium acidic salt coupling activator is in a solvent selected from acetonitrile, pyridine in acetonitrile, methylimidazole as well as their mixtures.

5. The method of claim 4, wherein the pyridinium acid salt coupling activator in acetonitrile.

6. The method of claim 1, wherein the stereodefined monomer of formula (1a) or (1b) is a oxazaphospholidine of formula (2a) or (2b):

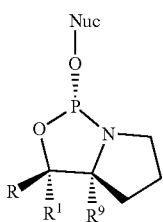
Formula 2a
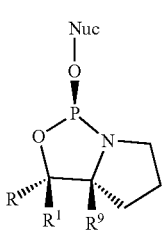
Formula 2b
wherein R, $R^1$, $R^9$ and Nuc are as according to formula (1a) or (1b).
7. The method of claim 1, wherein the sugar modification is selected from the group consisting of the following LNA sugar modifications:
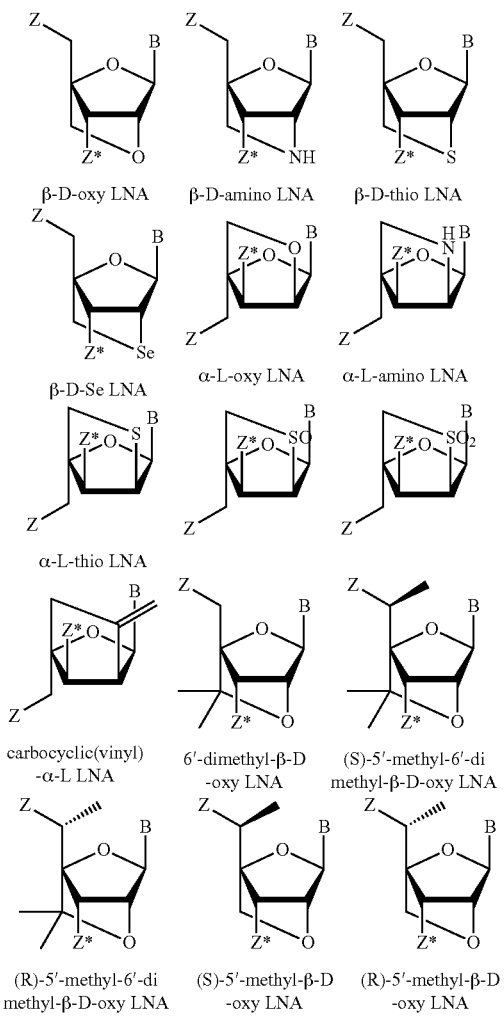
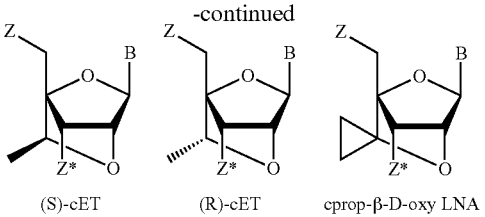
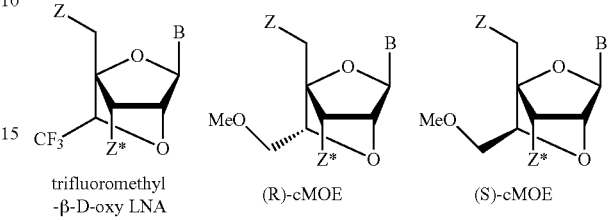
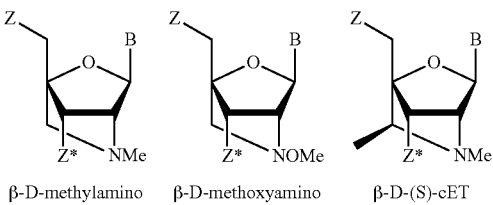
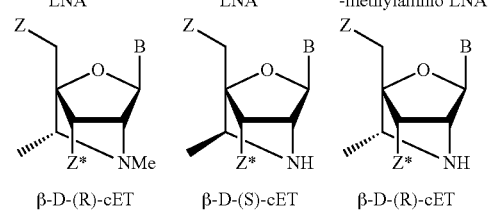
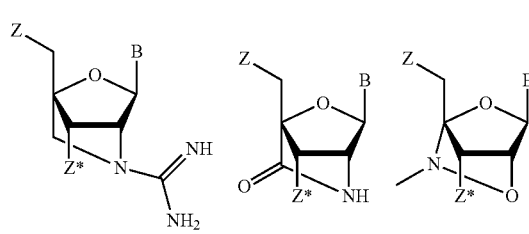
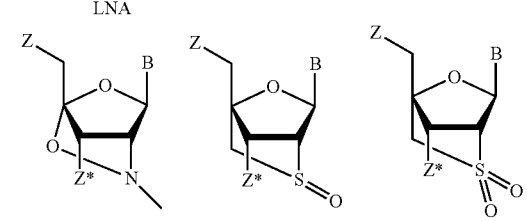
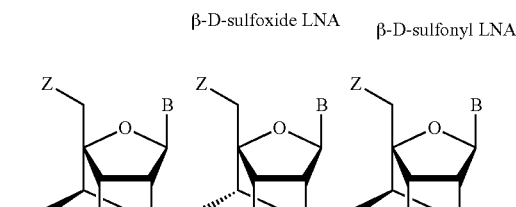
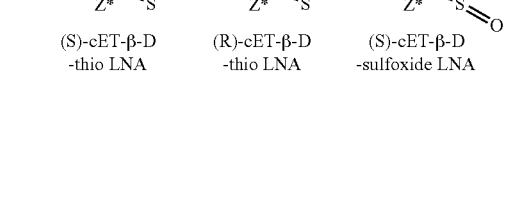

-continued

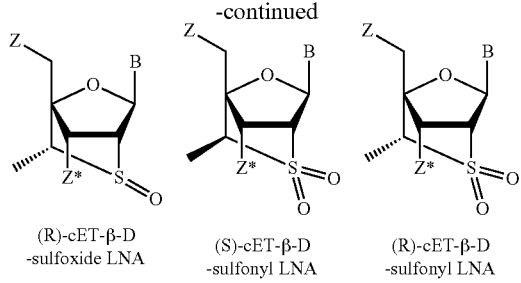
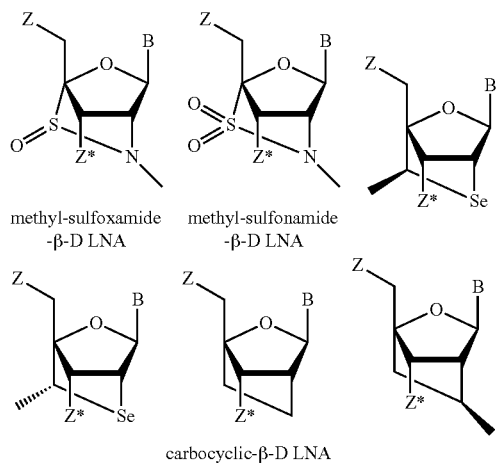
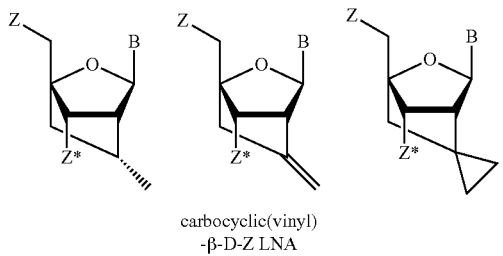
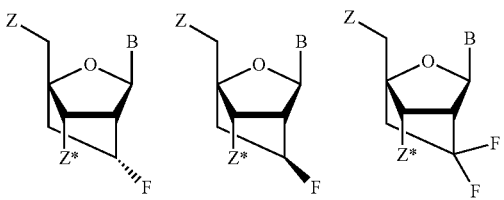
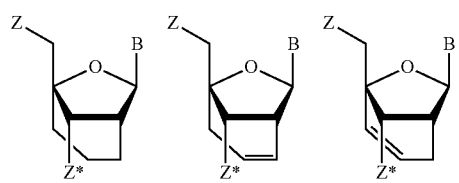
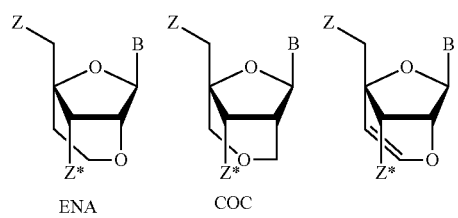

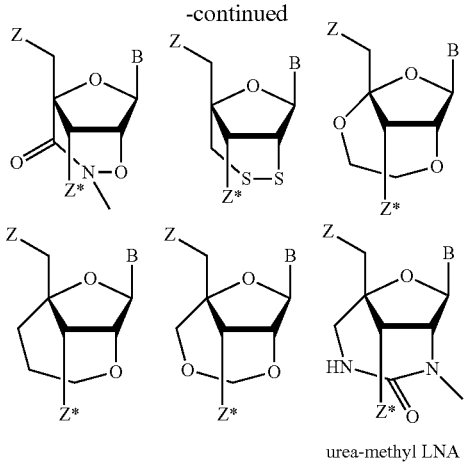

urea-methyl LNA wherein B is a nucleobase and Z and Z* are independently nucleotides.

8. The method of claim 7, wherein the sugar modification is selected from the group consisting of: beta-D-oxy-LNA, (R)-6'-methyl-beta-D-oxy LNA, (S)-6'-methyl-beta-D-oxy-LNA ((S)-cET) and ENA.

9. The method of claim 1, wherein the sugar modification is MOE:

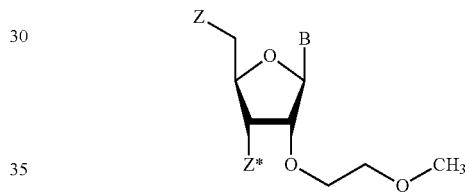

wherein B is a nucleobase and Z and Z* are independently nucleotides.

10. The method of claim 1, wherein the oxazaphospholidine monomer is of formula (3a) or (3b):

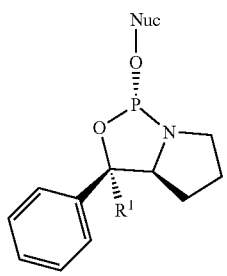

Formula 3a

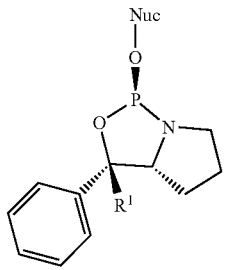

Formula 3b wherein Nuc is as defined herein, $R^1$ is H or methyl.

11. The method of claim 1, wherein the oxazaphospholidine monomer is of formula (3a) or (3b):

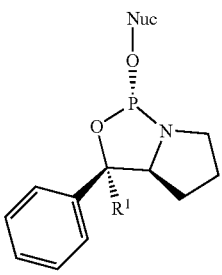

Formula 3a

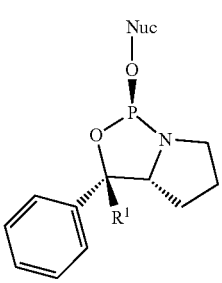

Formula 3b wherein Nuc is as defined herein, R¹ is H or methyl.

12. The method of claim 1, wherein the oxazaphospholidine monomer is of formula (10a) or (10b):

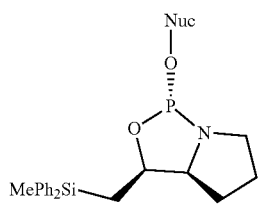

Formula 10a

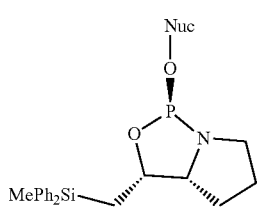

Formula 10b wherein Nuc is as defined herein, R¹ is H or methyl.

13. A composition comprising a pyridinium acidic salt activator, a solvent and an oxazaphospholidine monomer of formula (1a) or (1b) as defined in claim 1.

14. A method for the synthesis of stereodefined, sugar modified oligonucleotides comprising a step of coupling an oxazaphospholidine monomer of formula (1a) or (1b):

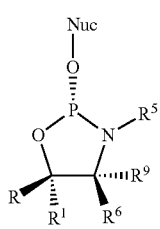

Formula 1a

-continued

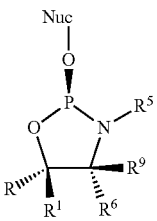

Formula 1b wherein Nuc is a nucleoside comprising a protected 5'-hydroxyl and is attached to the oxygen atom of Formula 1a or 1b via its 3' position;

R is selected from the groups consisting of nitro, halogen, cyano, silyl, sulfone, $C_{1-4}$ alkyl, $C_{1-4}$ alkylsulfone, $C_{6-14}$ arylsulfone, $C_{6-14}$ aryl, $C_{5-14}$ heteroaryl comprising one, two or three heteroatoms independently selected from O, N or S, each of the silyl, alkyl, aryl, heteroaryl moieties can be unsubstituted or substituted by one or more group(s) selected from the group consisting of: $C_{1-4}$ alkyl, $C_{6-14}$ aryl and $C_{1-4}$ alkoxy or silyl substituted by one or more substituent selected from $C_{1-4}$-alkyl and $C_{6-14}$ aryl;

R¹ is selected from hydrogen or $C_{1-4}$ alkyl; and

R⁵, R⁶ and R⁹ are independently selected from the group consisting of hydrogen, $C_{1-4}$ alkyl, $C_{5-6}$ cycloalkyl, $C_{6-14}$ aryl, $C_{5-14}$ heteroaryl comprising one, two or three heteroatoms independently selected from O, N or S, each of which alkyl, cycloalkyl, aryl or heteroaryl can be substituted by one, two or three substituents selected from the group consisting of $C_{1-4}$ alkyl, $C_{6-14}$ aryl and $C_{1-4}$, alkoxy:

or two of R⁵, R⁶ or R⁹ together form a heterocyclic ring comprising 3-7 carbon atoms, together with the N atom to which R⁵ is attached, wherein said heterocyclic ring can be substituted by one, two or three substituents selected from the group consisting of $C_{1-4}$ alkyl, $C_{6-14}$ aryl and $C_{1-4}$, alkoxy, with a nucleoside immobilized on a solid support wherein the coupling is performed in the presence of a pyridinium acidic salt coupling activator, wherein the pyridinium acidic salt coupling activator is pyridinium hydrochloride or pyridinium hydrobromide, wherein the pyridinium acidic salt coupling activator is pyridinium hydrobromide in a range from about 0.05 to about 0.50 M.

15. A method for the synthesis of stereodefined, sugar modified oligonucleotides comprising a step of coupling an oxazaphospholidine monomer of formula (1a) or (1b):

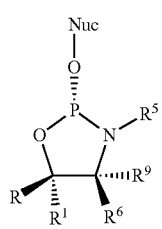

Formula 1a

Formula 1b

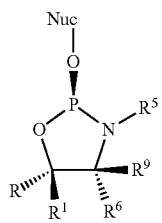

wherein Nuc is a nucleoside comprising a protected 5'-hydroxyl and is attached to the oxygen atom of Formula 1a or 1b via its 3' position;

R is selected from the groups consisting of nitro, halogen, cyano, silyl, sulfone, $C_{1-4}$ alkyl, $C_{1-4}$ alkylsulfone, $C_{6-14}$ arylsulfone, $C_{6-14}$ aryl, $C_{5-14}$ heteroaryl comprising one, two or three heteroatoms independently selected from O, N or S, each of the silyl, alkyl, aryl, heteroaryl moieties can be unsubstituted or substituted by one or more group(s) selected from the group consisting of: $C_{1-4}$ alkyl, $C_{6-14}$ aryl and $C_{1-4}$, alkoxy or silyl substituted by one or more substituent selected from $C_{1-4}$-alkyl and $C_{6-14}$ aryl;

$R^1$ is selected from hydrogen or $C_{1-4}$ alkyl; and $R^5$, $R^6$ and $R^9$ are independently selected from the group consisting of hydrogen, $C_{1-4}$ alkyl, $C_{5-6}$ cycloalkyl, $C_{6-14}$ aryl, $C_{5-14}$ heteroaryl comprising one, two or three heteroatoms independently selected from O, N or S, each of which alkyl, cycloalkyl, aryl or heteroaryl can be substituted by one, two or three substituents selected from the group consisting of $C_{1-4}$ alkyl, $C_{6-14}$ aryl and $C_{1-4}$, alkoxy:

or two of $R^5$, $R^6$ or $R^9$ together form a heterocyclic ring comprising 3-7 carbon atoms, together with the N atom to which $R^5$ is attached, wherein said heterocyclic ring can be substituted by one, two or three substituents selected from the group consisting of $C_{1-4}$ alkyl, $C_{6-14}$ aryl and $C_{1-4}$, alkoxy, with a nucleoside immobilized on a solid support wherein the coupling is performed in the presence of a pyridinium acidic salt coupling activator, wherein the pyridinium acidic salt coupling activator is pyridinium hydrochloride or pyridinium hydrobromide, wherein the pyridinium acidic salt coupling activator is pyridinium hydrobromide at about 0.25 M.

16. A method for the synthesis of stereodefined, sugar modified oligonucleotides comprising a step of coupling an oxazaphospholidine monomer of formula (1a) or (1b):

Formula 1a

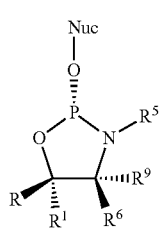

Formula 1b

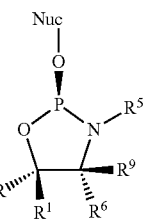

wherein Nuc is a nucleoside comprising a protected 5'-hydroxyl and is attached to the oxygen atom of Formula 1a or 1b via its 3' position;

R is selected from the groups consisting of nitro, halogen, cyano, silyl, sulfone, $C_{1-4}$ alkyl, $C_{1-4}$ alkylsulfone, $C_{6-14}$ arylsulfone, $C_{6-14}$ aryl, $C_{5-14}$ heteroaryl comprising one, two or three heteroatoms independently selected from O, N or S, each of the silyl, alkyl, aryl, heteroaryl moieties can be unsubstituted or substituted by one or more group(s) selected from the group consisting of: $C_{1-4}$ alkyl, $C_{6-14}$ aryl and $C_{1-4}$, alkoxy or silyl substituted by one or more substituent selected from $C_{1-4}$-alkyl and $C_{6-14}$ aryl;

$R^1$ is selected from hydrogen or $C_{1-4}$ alkyl; and $R^5$, $R^6$ and $R^9$ are independently selected from the group consisting of hydrogen, $C_{1-4}$ alkyl, $C_{5-6}$ cycloalkyl, $C_{6-14}$ aryl, $C_{5-14}$ heteroaryl comprising one, two or three heteroatoms independently selected from O, N or S, each of which alkyl, cycloalkyl, aryl or heteroaryl can be substituted by one, two or three substituents selected from the group consisting of $C_{1-4}$ alkyl, $C_{6-14}$ aryl and $C_{1-4}$, alkoxy:

or two of $R^5$, $R^6$ or $R^9$ together form a heterocyclic ring comprising 3-7 carbon atoms, together with the N atom to which $R^5$ is attached, wherein said heterocyclic ring can be substituted by one, two or three substituents selected from the group consisting of $C_{1-4}$ alkyl, $C_{6-14}$ aryl and $C_{1-4}$, alkoxy, with a nucleoside immobilized on a solid support wherein the coupling is performed in the presence of a pyridinium acidic salt coupling activator, wherein the pyridinium acidic salt coupling activator is pyridinium hydrochloride or pyridinium hydrobromide, wherein the pyridinium acidic salt coupling activator is pyridinium hydrochloride in a range from about 0.25 to about 1 M.

17. A method for the synthesis of stereodefined, sugar modified oligonucleotides comprising a step of coupling an oxazaphospholidine monomer of formula (1a) or (1b):

Formula 1a

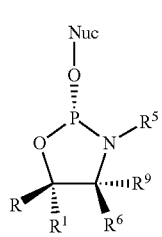

-continued

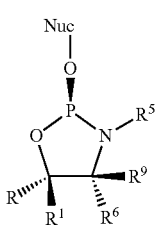

Formula 1b wherein Nuc is a nucleoside comprising a protected 5'-hydroxyl and is attached to the oxygen atom of Formula 1a or 1b via its 3' position;

R is selected from the groups consisting of nitro, halogen, cyano, silyl, sulfone, $C_{1-4}$ alkyl, $C_{1-4}$ alkylsulfone, $C_{6-14}$ arylsulfone, $C_{6-14}$ aryl, $C_{5-14}$ heteroaryl comprising one, two or three heteroatoms independently selected from O, N or S, each of the silyl, alkyl, aryl, heteroaryl moieties can be unsubstituted or substituted by one or more group(s) selected from the group consisting of: $C_{1-4}$ alkyl, $C_{6-14}$ aryl and $C_{1-4}$, alkoxy or silyl substituted by one or more substituent selected from $C_{1-4}$-alkyl and $C_{6-14}$ aryl;

$R^1$ is selected from hydrogen or $C_{1-4}$ alkyl; and $R^5$, $R^6$ and $R^9$ are independently selected from the group consisting of hydrogen, $C_{1-4}$ alkyl, $C_{5-6}$ cycloalkyl, $C_{6-14}$ aryl, $C_{5-14}$ heteroaryl comprising one, two or three heteroatoms independently selected from O, N or S, each of which alkyl, cycloalkyl, aryl or heteroaryl can be substituted by one, two or three substituents selected from the group consisting of $C_{1-4}$ alkyl, $C_{6-14}$ aryl and $C_{1-4}$, alkoxy:

or two of $R^5$, $R^6$ or $R^9$ together form a heterocyclic ring comprising 3-7 carbon atoms, together with the N atom to which $R^5$ is attached, wherein said heterocyclic ring can be substituted by one, two or three substituents selected from the group consisting of $C_{1-4}$ alkyl, $C_{6-14}$ aryl and $C_{1-4}$, alkoxy, with a nucleoside immobilized on a solid support wherein the coupling is performed in the presence of a pyridinium acidic salt coupling activator, wherein the pyridinium acidic salt coupling activator is pyridinium hydrochloride or pyridinium hydrobromide, wherein the pyridinium acidic salt coupling activator is pyridinium hydrochloride at about 0.50 M.

* * * * *